(12) United States Patent
Green et al.

(10) Patent No.: US 7,432,279 B2
(45) Date of Patent: Oct. 7, 2008

(54) 4,6-DIAMINO-[1,7]NAPHTHYRIDINE-3-CARBONITRILE INHIBITORS OF TPL2 KINASE AND METHODS OF MAKING AND USING THE SAME

(75) Inventors: Neal Jeffrey Green, Newton, MA (US); Lori Krim Gavrin, Woburn, MA (US); Neelu Kaila, Lexington, MA (US); Yonghan Hu, Acton, MA (US); Kristin Marie Janz, Arlington, MA (US); Jennifer R. Thomason, Revere, MA (US); Ariamala Gopalsamy, Mahwah, NJ (US); Steve Y. Tam, Wellesley, MA (US); Lih-Ling Lin, Concord, MA (US); John William Cuozzo, Natick, MA (US); Dennis William Powell, Cortlandt Manor, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/436,328

(22) Filed: May 18, 2006

(65) Prior Publication Data

US 2006/0276498 A1    Dec. 7, 2006

Related U.S. Application Data

(60) Provisional application No. 60/682,044, filed on May 18, 2005.

(51) Int. Cl.
*A01N 43/42* (2006.01)
*A61K 31/44* (2006.01)
*C07D 471/02* (2006.01)

(52) U.S. Cl. ........................ 514/300; 546/122
(58) Field of Classification Search ............... 546/122; 514/300
See application file for complete search history.

(56) References Cited

U.S. PATENT DOCUMENTS 6,355,636 B1 * 3/2002 Wissner et al. ............. 514/234.5
6,521,618 B2   2/2003 Boschelli et al.
6,548,496 B2   4/2003 Wissner et al.
6,689,772 B1   2/2004 Boschelli et al.

FOREIGN PATENT DOCUMENTS

WO    WO 00/66583    11/2000

OTHER PUBLICATIONS

Wissner et al., Bioorganic & Medicinal Chemistry Letters, "Syntheses and EGFR kinase inhibitory activity of 6-substituted-4-anilino [1,7] and [1,8] naphthyridine-3-carbonitriles", vol. 14, pp. 1411-1416.*
Beinke et al., Molecular and Cellular Biology, "NF-kB1 p105 Negatively regulates TPL-2 MEK Kinase Activity",2003, vol. 23, pp. 4739-4752.*
Tsatsanis et al., Oncogene, "Tpl-2 induces IL-2 expression in T-cell lines by triggering multiple signaling pathways that activate NFAT and NF-kB", vol. 17, 1998, pp. 2609-2618.*
Gavrin et al., "Inhibition of Tpl2 kinase and TNF-α production with 1,7-naphtyridine-3-carbonitriles: Synthesis and structure-activity relationships," Bioorganic & Medicinal Chemistry Letters, 15, 5288-92 (2005).
Green et al., "Inhibitors of Tumor Progression Loci-2 (Tpl2) Kinase and Tumor Necrosis Factor α (TNF-α) Production: Selectivity and in Vivo Antiinflammatory Activity of Novel 8-Substituted-4-anilino-6-aminoquinoline-3-carbonitriles," *J. Med. Chem.* 2007, 50, 4728-4745.
Hall et al., "Pharmacologic Inhibition of Tpl2 Blocks Inflammatory Responses in Primary Human Monocytes, Synoviocytes, and Blood," *J. Biol. Chem.* 2007, 282, 33295-33304.

* cited by examiner

*Primary Examiner*—D. Margaret Seaman
*Assistant Examiner*—Niloofar Rahmani
(74) *Attorney, Agent, or Firm*—Fish & Richardson P.C.

(57) ABSTRACT

The present invention provides compounds of formula (I):

and pharmaceutically acceptable salts thereof, wherein $R^1$, $R^2$, $R^3$, $R^4$, $R^5r^6$, m and n are defined as described herein. The invention also provides methods of making the compounds of formula (I), and methods of treating inflammatory diseases, such as rheumatoid arthritis, in a mammal comprising administering a therapeutically effective amount of a compound of formula (I) to the mammal.

31 Claims, No Drawings

4,6-DIAMINO-[1,7]NAPHTHYRIDINE-3-CARBONITRILE INHIBITORS OF TPL2 KINASE AND METHODS OF MAKING AND USING THE SAME

FIELD OF THE INVENTION

The invention relates to substituted 4,6-diamino-[1,7]naphthyridine-3-carbonitriles that are capable of inhibiting Tpl-2 kinase and to methods for the preparation of the substituted 4,6-diamino-[1,7]naphthyridine-3-carbonitriles. The 4,6-diamino-[1,7]naphthyridine-3-carbonitriles of the present invention are useful for the treatment of inflammatory diseases, such as rheumatoid arthritis.

BACKGROUND

Protein kinases are a class of enzymes that catalyze the transfer of a phosphate group from ATP to a tyrosine, serine, threonine, or histidine residue located on a protein substrate, many of which play a role in normal cell growth. Protein tyrosine kinases (PTKs) play a key role in signal transduction pathways that regulate cell division and differentiation. Certain growth factor receptor kinases have been identified as markers for a poor prognosis in many human cancers if they are overexpressed. See Hickey e al. *J. Cancer,* 1994, 74:1693.

Similar to PTKs, serine/threonine kinases are also involved in the regulation of cell growth. The MEK kinase Tpl-2 (also known as Cot and MAP3K8) is a serine/threonine kinase that has been shown to be a protooncogene when it is cleaved at its C-terminus. See Beinke et al., *Mol. Cell Biol.,* 2003, 23:4739-4752.

Tpl-2 is known to be upstream in the MEK-ERK pathway and is essential for LPS induced tumor necrosis factor-α (TNF-α) production, as demonstrated by the Tpl2 knockout mouse (Tsichlis et. al. *EMBO J.,* 1996, 15, 817). Tpl-2 is also required for TNF-α signaling (i.e. the cellular response to ligation of the TNF-α receptor). TNF-α is a pro-inflammatory cytokine that is involved in inflammation in a number of disease states, most notably in the autoimmune disease rheumatoid arthritis (RA). A protein therapeutic ENBREL/etanercept (sTNRRα) is currently available to patients with RA. However, an orally available small molecule that inhibits TNF-α synthesis and/or signaling is desirable. Tpl2 is not inhibited by staurosporine and it is the only human kinase that contains a proline instead of a conserved glycine in the glycine-rich ATP binding loop. These unique features of Tpl2 may increase the potential for discovering a selective inhibitor of the enzyme.

Heretofore, there have not been described [1,7]naphthyridines that bind to and inhibit serine/threonine protein kinases and inhibit TNF-α synthesis and/or signaling that are useful in the treatment of inflammatory diseases. The present invention provides 4,6-diamino-[1,7]naphthyridine-3-carbonitriles that are inhibitors of the serine/threonine kinase Tpl-2 and can be used to treat inflammatory diseases, such as RA. The invention also provides methods of making the 4,6-diamino-[1,7]naphthyridine-3-carbonitriles.

SUMMARY OF THE INVENTION

The present invention provides compounds of formula (I):

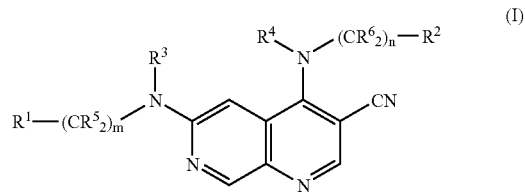

and pharmaceutically acceptable salts thereof, wherein $R^1$, $R^2$, $R^3$, $R^4$, $R^5$, $R^6$, m and n are defined as described herein. The invention also provides methods of making the compounds of formula (I), and methods of treating or preventing inflammatory diseases, such as rheumatoid arthritis, comprising administering a therapeutically effective amount of a compound of formula (I) to a mammal in need thereof.

DETAILED DESCRIPTION

The invention provides compounds of formula (I):

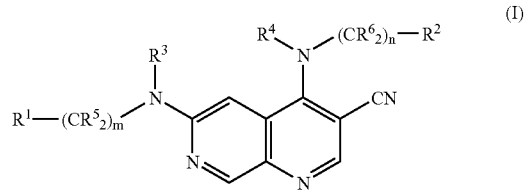

wherein:
$R^1$ is selected from the group consisting of $C_{3-10}$ cycloalkyl, aryl, 3-10 membered cycloheteroalkyl, and heteroaryl, each optionally substituted with 1-4 moieties selected from the group consisting of:
a) halogen, b) CN, c) $NO_2$, d) $N_3$, e) $OR^7$, f) $NR^8R^9$, g) oxo, h) thioxo, i) $S(O)_pR^7$, j) $SO_2NR^8R^9$, k) $C(O)R^7$, l) $C(O)OR^7$, m) $C(O)NR^8R^9$, n) $Si(C_{1-6}\ alkyl)_3$, o) $C_{1-6}$ alkyl, p) $C_{2-6}$ alkenyl, q) $C_{2-6}$ alkynyl, r) $C_{1-6}$ alkoxy, s) $C_{1-6}$ alkylthio, t) $C_{1-6}$ haloalkyl, u) $C_{3-10}$ cycloalkyl, v) aryl, w) 3-10 membered cycloheteroalkyl, and x) heteroaryl,
wherein any of o)-x) optionally is substituted with 1-4 $R^{10}$ groups;

alternatively, $R^1$ is selected from the group consisting of halogen, $C_{1-6}$ alkyl optionally substituted with 1-4 $R^{12}$ groups, $C_{1-6}$ haloalkyl, $OR^7$, $NR^8R^9$, $S(O)_pR^7$, $SO_2NR^8R^9$, $C(O)R^7$, $C(O)OR^7$, $C(O)NR^8R^9$ and $N_3$;

$R^2$ is selected from the group consisting of $C_{3-10}$ cycloalkyl, aryl, 3-10 membered cycloheteroalkyl, and heteroaryl, each optionally substituted with 1-4 moieties selected from the group consisting of:
a) halogen, b) CN, c) $NO_2$, d) $N_3$, e) $OR^7$, f) $NR^8R^9$, g) oxo, h) thioxo, i) $S(O)_pR^7$, j) $SO_2NR^8R^9$, k) $C(O)R^7$, l) $C(O)OR^7$, m) $C(O)NR^8R^9$, n) $Si(C_{1-6}\ alkyl)_3$, o) $C_{1-6}$ alkyl, p) $C_{2-6}$ alkenyl, q) $C_{2-6}$ alkynyl, r) $C_{1-6}$ alkoxy, s) $C_{1-6}$ alkylthio, t) $C_{1-6}$ haloalkyl, u) $C_{3-10}$ cycloalkyl, v) aryl, w) 3-10 membered cycloheteroalkyl, and x) heteroaryl, wherein any of o)-x) optionally is substituted with 1-4 $R^{10}$ groups;

alternatively, $R^2$ is selected from the group consisting of halogen, $C_{1-6}$ alkyl optionally substituted with 1-4 $R^{10}$ groups, $C_{1-6}$ haloalkyl, $NR^8R^9$, $OR^7$, $C(O)OR^7$, $C(O)NR^8R^9$, $S(O)_pR^7$ and $N_3$;

$R^3$ and $R^4$ independently are selected from the group consisting of:
a) H, b) $C(O)R^7$, c) $C(O)OR^7$, d) $C(O)NR^8R^9$, e) $C_{1-6}$ alkyl, f) $C_{2-6}$ alkenyl, g) $C_{2-6}$ alkynyl, h) $C_{1-6}$ haloalkyl, i) $C_{3-10}$ cycloalkyl, j) aryl, k) 3-10 membered cycloheteroalkyl, and l) heteroaryl, wherein any of e)-l) optionally is substituted with 1-4 $R^{10}$ groups;

$R^5$ and $R^6$ at each occurrence independently are selected from the group consisting of:
a) H, b) halogen, c) $OR^7$, d) $NR^8R^9$, e) $C_{1-6}$ alkyl, f) $C_{2-6}$ alkenyl, g) $C_{2-6}$ alkynyl, h) $C_{1-6}$ haloalkyl, and i) aryl;

alternatively, any two $R^5$ and $R^6$ groups and the carbon to which they are bonded may form a carbonyl group;

$R^7$ at each occurrence is selected from the group consisting of:
a) H, b) $C(O)R^{11}$, c) $C(O)OR^{11}$, d) $C(O)NR^{11}R^{12}$, e) $C_{1-6}$ alkyl, f) $C_{2-6}$ alkenyl, g) $C_{2-6}$ alkynyl, h) $C_{1-6}$ haloalkyl, i) $C_{3-10}$ cycloalkyl, j) aryl, k) 3-10 membered cycloheteroalkyl, and l) heteroaryl;

wherein any of e)-l) optionally is substituted with 1-4 $R^{13}$ groups;

$R^8$ and $R^9$ at each occurrence independently are selected from the group consisting of:
a) H, b) $OR^{11}$, c) $SO_2R^{11}$, d) $SO_2NR^8R^9$, e) $C(O)R^{11}$, f) $C(O)OR^{11}$, f) $C(O)NR^{11}R^{12}$, g) $C_{1-6}$ alkyl, h) $C_{2-6}$ alkenyl, i) $C_{2-6}$ alkynyl, j) $C_{1-6}$ haloalkyl, k) $C_{3-10}$ cycloalkyl, l) aryl, m) 3-10 membered cycloheteroalkyl, and n) heteroaryl;

wherein any of g)-n) optionally is substituted with 1-4 $R^{13}$ groups;

$R^{10}$ at each occurrence independently is selected from the group consisting of:
a) halogen, b) CN, c) $NO_2$, d) $N_3$, e) $OR^7$, f) $NR^8R^9$, g) oxo, h) thioxo, i) $S(O)_gR^7$, j) $SO_2NR^8R^9$, k) $C(O)R^7$, l) $C(O)OR^7$, m) $C(O)NR^8R^9$, n) $Si(C_{1-6}$ alkyl$)_3$, o) $C_{1-6}$ alkyl, p) $C_{2-6}$ alkenyl, q) $C_{2-6}$ alkynyl, r) $C_{1-6}$ alkoxy, s) $C_{1-6}$ alkylthio, t) $C_{1-6}$ haloalkyl, u) $C_{3-10}$ cycloalkyl, v) aryl, w) 3-10 membered cycloheteroalkyl, and x) heteroaryl, wherein any of o)-x) optionally is substituted with 1-4 $R^{13}$ groups;

$R^{11}$ and $R^{12}$ at each occurrence independently are selected from the group consisting of:
a) H, b) $C_{1-6}$ alkyl, c) $C_{2-6}$ alkenyl, d) $C_{2-6}$ alkynyl, e) $C_{1-6}$ haloalkyl, f) $C_{3-10}$ cycloalkyl, g) aryl, h) 3-10 membered cycloheteroalkyl, and i) heteroaryl, wherein any of b)-j) optionally is substituted with 1-4 $R^{13}$ groups;

$R^{13}$ at each occurrence independently is selected from the group consisting of:
a) halogen, b) CN, c) $NO_2$, d) $N_3$, e) OH, f) O—$C_{1-6}$alkyl, g) $NH_2$, h) $NH(C_{1-6}$alkyl), i) $N(C_{1-6}$ alkyl$)_2$, j) NH(aryl), k) NH(cycloalkyl), l) NH(heteroaryl), m) NH(cycloheteroalkyl), n) oxo, o) thioxo, p) SH, q) $S(O)_p$—$C_{1-6}$alkyl, r) C(O)—$C_{1-6}$alkyl, s) C(O)OH, t) C(O)O—$C_{1-6}$ alkyl, u) $C(O)NH_2$, v) $C(O)NHC_{1-6}$ alkyl, w) $C(O)N(C_{1-6}$ alkyl$)_2$, x) $C_{1-6}$ alkyl, y) $C_{2-6}$ alkenyl, z) $C_{2-6}$ alkynyl, aa) $C_{1-6}$ alkoxy, bb) $C_{1-6}$ alkylthio, cc) $C_{1-6}$ haloalkyl, dd) $C_{3-10}$ cycloalkyl, ee) aryl, ff) 3-10 membered cycloheteroalkyl, and gg) heteroaryl, wherein any $C_{1-6}$ alkyl, $C_{2-6}$ alkenyl, $C_{2-6}$ alkynyl, $C_{3-10}$ cycloalkyl, aryl, 3-10 membered cycloheteroalkyl, or heteroaryl, alone as a part of another moiety, optionally is substituted with one or more moieties selected from the group consisting of halogen, CN, $NO_2$, OH, O—$C_{1-6}$ alkyl, $NH_2$, $NH(C_{1-6}$alkyl), $N(C_{1-6}$alkyl$)_2$, NH(aryl), NH(cycloalkyl), NH(heteroaryl), NH(cycloheteroalkyl), oxo, thioxo, SH, $S(O)_p$—$C_{1-6}$alkyl, C(O)—$C_{1-6}$alkyl, C(O)OH, C(O)O—$C_{1-6}$alkyl, $C(O)NH_2$, $C(O)NHC_{1-6}$ alkyl, $C(O)N(C_{1-6}$ alkyl$)_2$, $C_{1-6}$ alkyl, $C_{2-6}$ alkenyl, $C_{2-6}$ alkynyl, $C_{1-6}$ alkoxy, $C_{1-6}$ alkylthio, $C_{1-6}$ haloalkyl, $C_{3-10}$ cycloalkyl, aryl, 3-10 membered cycloheteroalkyl, and heteroaryl;

m is 0, 1, 2, 3, or 4;
n is 0 or 1; and
p is 0, 1, or 2;

or a pharmaceutically acceptable salt thereof, provided that the compound of Formula (I) does not comprise:

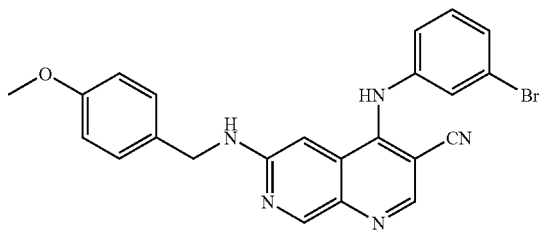

4-(3-Bromo-phenylamino)-6-(4-methoxy-benzylamino)-[1,7]naphthyridine-3-carbonitrile, or

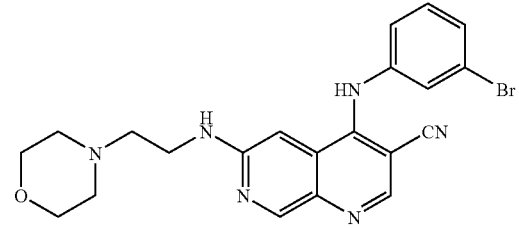

4-(3-Bromo-phenylamino)-6-(2-morpholin-4-yl-ethylamino)-[1,7]naphthyridine-3-carbonitrile.

Incertain embodiments, $R^1$ is a 5 or 6 membered heteroaryl, such as imidazole or pyridine (e.g., piridin-3-yl). In other embodiments, $R^1$ is a 5 or 6 membered cycloheteroalkyl, such as piperidine or morpholine. Alternatively, $R^1$ may be phenyl optionally substituted with, for example, $OR^7$ (e.g., $OCH_3$) or $S(O)_pR^7$ (e.g., $SO_2CH_3$).

In some embodiments, m is 1 or 2.

$R^2$ may be phenyl optionally substituted with 1-2 halogens, for example 3-chloro-4-florophenyl. Alternatively, the phenyl may be substituted with benzyl, S-phenyl or O-phenyl. In other embodiments, $R^2$ is cycloalkyl, such as cyclopropyl, cyclopentyl, cyclohexyl, or cycloheptyl.

In some embodiments, n is 0.

$R^3$ may be, for instance, H or $C_{1-6}$ alkyl.

Examples of $R^4$ include H and $C_{1-6}$ alkyl.

In some embodiments, when m is 2, 3, or 4, and $R^1$ is morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran or

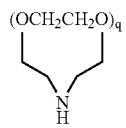

wherein q is 1-4, then $R^2$ is not pyridine, pyrimidine, phenyl, bicyclic aryl, or bicyclic heteroaryl substituted with 1-3 groups selected from the group consisting of:
  a) halogen, b) CN, c) $NO_2$, d) $OR^7$, e) $NR^8R^9$, f) $SO_2NR^8R^9$, g) $C(O)R^7$, h) $C(O)OR^7$, i) $C_{1-6}$ alkyl, j) $C_{2-6}$ alkenyl, k) $C_{2-6}$ alkynyl, l) $C_{1-6}$ alkoxy, m) $C_{1-6}$ alkylthio, n) $C_1$ haloalkyl, o) —$NR^{14}(CH_2)_r$—X, p)—$(CH_2)_r NR^{14}$—X, q) —$O(CH_2)_r$—X, r)—$(CH_2)_r O$—X, s) —$S(CH_2)_r$—X, t) —$(CH_2)_r S$—X, and u) —$(CH_2)_r$—X, wherein
  $R^{14}$ is H, $C_{1-6}$ alkyl or $C(O)$—$C_{1-6}$ alkyl;
  X is phenyl or a 5-6 membered heteroaryl ring; and
  r is 0-3.

The invention also includes intermediates of the compounds described herein having the formula (II):

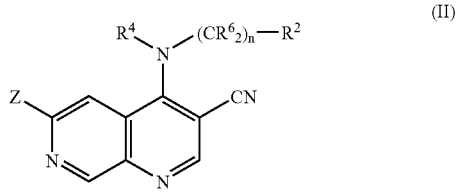

wherein Z is halogen, $C_{1-6}$ alkyl optionally substituted with 1-4 $R^{12}$ groups, $C_{1-6}$ haloalkyl, $OR^7$, $NR^8R^9$, $S(O)_pR^7$, $SO_2NR^8R^9$, $C(O)R^7$, $C(O)OR^7$, $C(O)NR^8R^9$ or $N^3$, and $R^2$, $R^4$, $R^6$, $R^7$, $R^8$, and $R^9$ are defined as described above.

Also provided in accordance with the present invention are pharmaceutically acceptable salts, and prodrugs, of the compounds disclosed herein.

The compounds of the present invention are useful for the treatment of disease conditions mediated by Tpl-2, such as rheumatoid arthritis (RA), juvenile RA, psoriatic arthritis, ankylosing spondylitis, and osteoarthritis and for the alleviation of symptoms thereof. Accordingly, the present invention further provides methods of treating these diseases and disorders using the compounds described herein. In some embodiments, the methods include identifying a mammal having a disease or disorder mediated by Tpl-2, and providing to the mammal an effective amount of a compound as described herein.

In further embodiments, the methods are provided for alleviating a symptom of a disease or disorder mediated by Tpl-2. In some embodiments, the methods include identifying a mammal having a symptom of a disease or disorder mediated by Tpl-2, and providing to the mammal an amount of a compound as described herein effective to ameliorate (i.e., lessen the severity of) the symptom.

Pharmaceutically acceptable salts of the compounds of Formula (I) having an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example, salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, or camphorsulfonic acid, or other known pharmaceutically acceptable acids.

The present invention also includes prodrugs of the compounds described herein. As used herein, "prodrug" refers to a moiety that releases a compound of the invention when administered to a mammalian subject. Prodrugs can be prepared by modifying functional groups present in the compounds in such a way that the modifications are cleaved, either by routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a mammalian subject, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

The present invention provides pharmaceutical compositions comprising at least one compound according to the invention and one or more pharmaceutically acceptable carriers, excipients, or diluents. Examples of such carriers are well known to those skilled in the art and are prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable. Supplementary active ingredients can also be incorporated into the compositions.

The compounds of the invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antiinflammatory agents. Oral formulations containing the active compounds of this invention may comprise any conventionally used oral form, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets may contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, or a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Examples of liquid carriers for oral and parenteral administration include water (particularly containing additives as described above, e.g. cellulose derivatives, such as a sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally, i.e., administered across the surface of the body and the inner linings of bodily passages including epithelial and mucosal tissues. Such administrations may be carried out using the present compounds or pharmaceutically acceptable salts thereof, in lotions, creams, foams, patches, suspensions, solutions, and suppositories (rectal and vaginal). Topical formaulations that deliver the compounds of the invention through the epidermis may be useful for localized treatment of inflammation and arthritis.

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

Lipid formulations or nanocapsules may be used to introduce the compounds of the present invention into host cells either in vitro or in vivo. Lipid formulations and nanocapsules may be prepared by methods known in the art.

In order to increase the effectiveness of the compounds of the present invention, it may be desirable to combine these compositions with other agents effective in the treatment of the target disease. For inflammatory diseases, other agents effective in their treatment, and particularly in the treatment of rheumatoid arthritis, may be administered with the compounds of the present invention. For cancer, additional anticancer agents may be administered. The other agents may be administered at the same time or at different times than the compounds of the present invention.

As used herein, "halo" or "halogen" includes fluoro, chloro, bromo, and iodo.

As used herein, "oxo" refers to a double-bonded oxygen (i.e., =O).

As used herein, the term "alkyl" refers to a straight-chain or branched saturated hydrocarbon group. Alkyl groups can contain from 1 to about 20, 1 to about 10, 1 to about 8, 1 to about 6, 1 to about 4, or 1 to about 3 carbon atoms. Alkyl groups preferably contain 1 to 6 carbon atoms. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. Alkyl groups can be substituted with up to four independently selected $R^{12}$ groups, as described herein.

As used herein, "alkenyl" refers to a straight-chain or branched alkyl group as defined above having one or more double carbon-carbon bonds. Alkenyl groups preferably contain 2 to 6 carbon atoms. Examples of alkenyl groups include ethenyl, propenyl, butenyl, pentenyl, hexenyl, butadienyl, pentadienyl, hexadienyl, and the like. Alkenyl groups can be substituted with up to four independently selected $R^{12}$ groups, as described herein.

As used herein, "alkynyl" refers to a straight-chain or branched alkyl group as defined above having one or more triple carbon-carbon bonds. Alkynyl groups preferably contain 2 to 6 carbon atoms. Examples of alkynyl groups include ethynyl, propynyl, butynyl, pentynyl, and the like. Alkynyl groups can be substituted with up to four independently selected $R^{12}$ groups, as described herein.

As used herein, "alkoxy" refers to an —O-alkyl group, wherein alkyl is as defined above. Alkoxy groups preferably contain 1 to 6 carbon atoms. Examples of alkoxy groups include methoxy, ethoxy, propoxy (e.g., n-propoxy and isopropoxy), t-butoxy, and the like. Alkoxy groups can be substituted with up to four independently selected $R^{12}$ groups, as described herein.

As used herein, "alkylthio" refers to an —S-alkyl group, wherein alkyl is as defined above. Alkylthio groups preferably contain 1 to 6 carbon atoms. Alkylthio groups can be substituted with up to four independently selected $R^{12}$ groups, as described herein.

As used herein, "haloalkyl" refers to an alkyl group, as defined above, having one or more halogen substituents. Haloalkyl groups preferably contain 1 to 6 carbon atoms. Examples of haloalkyl groups include $CF_3$, $C_2F_5$, $CHF_2$, $CCl_3$, $CHCl_2$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl."

As used herein, "cycloalkyl" refers to non-aromatic carbocyclic groups including cyclized alkyl, alkenyl, and alkynyl groups. Cycloalkyl groups can be monocyclic (e.g., cyclohexyl) or poly-cyclic (e.g. fused, bridged, or spiro ring systems), wherein the carbon atoms are located inside or outside of the ring system. Cycloalkyl groups preferably contain 3 to 10 carbon atoms. Any suitable ring position of the cycloalkyl moiety may be covalently linked to the defined chemical structure. Examples of cycloalkyl groups include cyclopropyl, cyclopropylmethyl, cyclobutyl, cyclopentyl, cyclohexyl, cyclohexylmethyl, cyclohexylethyl, cycloheptyl, cyclopentenyl, cyclohexenyl, cyclohexadienyl, cycloheptatrienyl, norbornyl, norpinyl, norcarnyl, adamantyl, spiro[4.5]deanyl, homologs, isomers, and the like. Also included in the definition of cycloalkyl are moieties that have one or more aromatic rings fused (i.e., having a bond in common with) to the cycloalkyl ring, for example, benzo derivatives of cyclopentane (indanyl), cyclohexane (tetrahydronaphthyl), and the like. Cycloalkyl groups can be substituted with up to four independently selected $R^{12}$ groups, as described herein.

As used herein, "aryl" refers to $C_{6-20}$ aromatic monocyclic or polycyclic hydrocarbons such as, for example, phenyl, 1-naphthyl, 2-naphthyl anthracenyl, phenanthrenyl, and the like. Aryl groups preferably contain 6 to 14 carbon atoms. Any suitable ring position of the aryl moiety may be covalently linked to the defined chemical structure. Aryl groups can be substituted with up to four independently selected $R^{12}$ groups, as described herein.

As used herein, "heteroaryl" refers to monocyclic or polycyclic aromatic ring systems having from 5 to 20 ring atoms and containing 1-3 ring heteroatoms selected from oxygen (O), nitrogen (N) and sulfur (S). Generally, heteroaryl rings do not contain O—O, S—S, or S—O bonds. Heteroaryl groups include monocyclic heteroaryl rings fused to a phenyl ring. The heteroaryl group may be attached to the defined chemical structure at any heteroatom or carbon atom that results in a stable structure. Examples of heteroaryl groups include, for example:

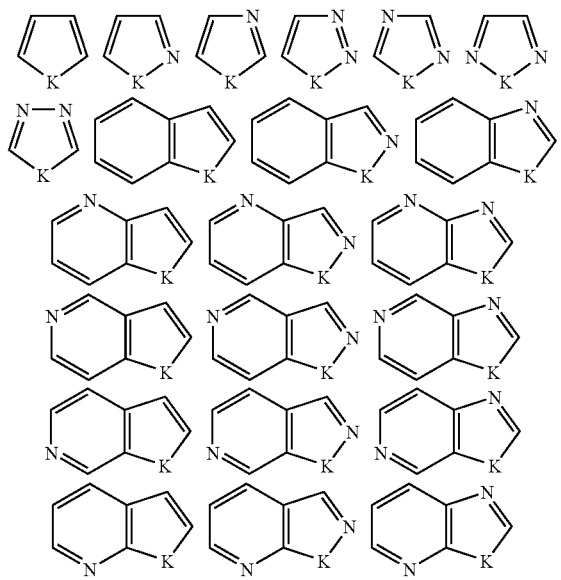

wherein K is defined as O, S, N or NR$^8$. One or more N or S in a heteroaryl ring may be oxidized (e.g., pyridine N-oxide). Examples of heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, 2-methylquinoline-4-yl, 1-H-1,2,3-benzotriazol-1-yl, 1-H-benzimidazol-5-yl, 2,1,3-benzoxadiazol-5-yl, benzoxazole, benzimidazolyl, benzofuranyl, benzothiofuranyl, benzothiophenyl, benzoxazolyl, benzthiazolyl, benztriazolyl, benztetrazolyl, benzo[c]isoxazolyl, benzo[d]isoxazolyl, benzo[c]isothiazolyl, benzo[d]isothiazolyl, cinnolinyl, 1H-indazolyl, 2H-indazolyl, indolizinyl, indolyl, isobenzofuranyl, isoindolyl, isoquinolinyl, naphthyridinyl, phthalazinyl, pteridinyl, purinyl, oxazolopyridinyl, thiazolopyridinyl, imidazopyridinyl, furopyridinyl, thienopyridinyl, pyridopyrimidine, pyridopyrazine, pyridopyridazine, quinazolinyl, quinolinyl, quinoxalinyl, thienothiazolyl, thienoxazolyl, and thienoimidazolyl. Heteroaryl groups can be substituted with up to four independently selected R$^{12}$ groups as described herein.

As used herein, "cycloheteroalkyl" refers to a non-aromatic cycloalkyl group that contains at least one ring heteroatom selected from O, N and S, and optionally contains one or more double or triple bonds. Cycloheteroalkyl groups preferably contain 3 to 10 ring atoms, 1-3 of which are heteroatoms selected from O, S, and N. One or more N or S in a cycloheteroalkyl ring may be oxidized (e.g., thiomorpholine S-oxide, thiomorpholine S,S-dioxide). Examples of cycloheteroalkyl groups include morpholine, thiomorpholine, pyran, imidazolidine, imidazoline, oxazolidine, pyrazolidine, pyrazoline, pyrrolidine, pyrroline, tetrahydrofuran, tetrahydrothiophene, piperidine piperazine, and the like. Cycloheteroalkyl groups can be optionally substituted with up to four independently selected R$^{14}$ groups as described herein. Nitrogen atoms of cycloheteroalkyl groups can bear a substituent, for example an R$^5$ group, as described herein. Also included in the definition of cycloheteroalkyl are moieties that have one or more aromatic rings fused (i.e., having a bond in common with) to the cycloheteroalkyl ring, for example, benzimidazolinyl, chromanyl, chromenyl, indolinetetrahydorquinolinyl, and the like. Cycloheteroalkyl groups can also contain one or more oxo groups, such as phthalimide, piperidone, oxazolidinone, pyrimidine-2,4(1H,3 H)-dione, and pyridin-2(1 H)-one, and the like.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The compounds of the present invention can contain an asymmetric atom (also referred as a chiral center), and some of the compounds can contain one or more asymmetric atoms or centers, which can thus give rise to optical isomers (enantiomers) and diastereomers. The present invention includes such optical isomers (enantiomers) and diastereomers (geometric isomers); as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. The present invention also encompasses cis and trans isomers of compounds containing alkenyl moieties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Compounds of the invention may be synthesized, for example, according to Scheme I below.

As shown in Scheme I, 6-Chloro-3-nitropyridine a is converted to 6-fluoro-3-nitropyridine b with a reagent such as potassium fluoride or sodium fluoride in a solvent such as DMSO. The nitro group in b is reduced to an amino group with a reducing agent (e.g., tin chloride, Raney Nickel or palladium on carbon) in the presence of hydrogen gas to produce 6-Chloro-3-aminopyridine c, which is protected in the form of a carbamate using an acylating reagent (e.g., tert-butoxy carbonyl anhydride) in an alcoholic solvent such as tert-butanol to give a protected amine, such as the Boc-protected amine d. Deprotonation with a base such as n-BuLi or lithium diisopropylamide, followed by the addition of carbon dioxide gas yields a carboxylic acid, which is esterified with an esterification reagent (e.g., diazomethane or trimethylsilyldiazomethane) and an alcohol (e.g., methanol or ethanol) to yield an ester, such as the methyl ester e. The ester of e is then converted to a β-ketonitrile with the addition of the anion of acetonitrile (generated by treating acetonitrile with a base such as n-butyllithium or lithium diisopropylamide) in a solvent such as ether to give f. Condensation of f using, for example, dimethylformamide-dimethylacetal in a solvent such as dimethylformamide, yields the naphthrydine ring g. Chlorination of g using, for example, oxalyl chloride, phosphorus oxychloride or thionyl chloride (neat or in a solvent) yields the naphthrydine h. The amine at the C-4 position is added by heating h and an amine having the formula HR$^4$N (CR$^6{}_2$)$_n$R$^2$ in a solvent such as ethanol, DMF, THF, or 1,2-dimethoxyethane. Finally, the resulting 3-cyano-4-amino-6-fluoro-[1,7]naphthyrine i is converted to a compound of formula (I) by heating with an amine having the formula HR$^3$N(CR$^5{}_2$)$_m$R$^1$, in a solvent such as DMSO, DMF, DMA, THF, ethanol or pyridine.

EXAMPLES

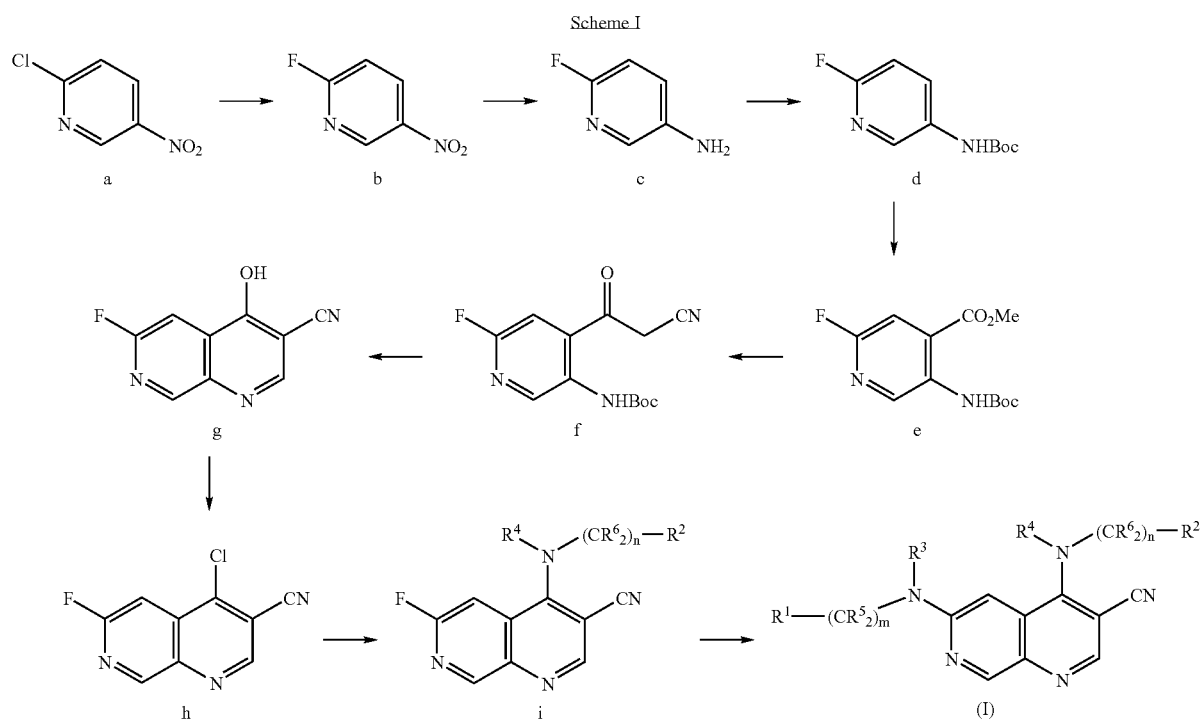

The following describes the preparation of representative compounds of this invention in greater detail. The following examples are offered for illustrative purposes, and are not intended to limit the invention in any manner. Those of skill in the art will readily recognize a variety of parameters that can be changed or modified to yield essentially the same results.

Mass spectral data is reported as the mass-to-charge ratio, m/z; and for high resolution mass spectral data, the calculated and experimentally found masses, [M+H]$^+$, for the neutral formulae M are reported. Nuclear magnetic resonance data is reported as δ in parts per million (ppm) downfield from the standard (tetramethylsilane), along with the solvent, nucleus, and field strength parameters. The spin-spin homonuclear coupling constants are reported as J values in hertz; and the multiplicities are reported as a: s, singlet; d, doublet; t, triplet; q, quartet; quintet; or br, broadened.

Example 1

4-(3-chloro-4-fluorophenylamino)-6-(pyridin-3-ylm-ethylamino)-1,7-naphthyridine-3-carbonitrile In a microwave vial, 4-chloro-6-fluoro-1,7-naphthyridine-3-carbonitrile (1.25 g, 6.02 mmol, prepared as described in Wissner et. al., *Bioorg. Med. Chem. Lett.*, 14, 2004, 1411-1416) and 3-chloro-4-fluoroaniline (0.96 g, 6.6 mmol) were taken up in DME. The vial was crimp-sealed and heated in a microwave reactor at 140° C. for 10 minutes. This was repeated with a second batch of reagents. The contents of the two vials were transferred together to a separatory funnel and partitioned between EtOAc and 5% $Na_2CO_3$, and the aqueous layer extracted two additional times with EtOAc. The combined organic extracts were washed with brine, dried over anhydrous $MgSO_4$, filtered and evaporated to give 4-(3-chloro-4-fluorophenylamino)-6-fluoro-1,7-naphthyridine-3-carbonitrile of sufficient purity to be used directly in the next step (3.78 g, 99% yield): $^1$H NMR (400 MHz, DMSO-$D_6$) δ 7.32-7.49 (m, 1 H) 7.53 (t, J=9.0 Hz, 1 H) 7.72 (dd, J=6.3, 2.3 Hz, 1 H) 8.16 (s, 1 H) 8.69 (s, 1 H) 9.08 (s, 1 H) 10.14 (s, 1 H).

The product of the first step (0.78 g, 2.5 mmol) was taken up in 3-(aminomethyl)pyridine (5.0 mL, 5.3 g, 49 mmol) in a microwave vial. The sealed vial was heated in a microwave reactor at 190° C. for 5 minutes (TLC analysis showed complete consumption of starting material). This was repeated 4 times, with 1.13 g, 0.78 g, 0.78 g and 0.31 g 6-fluoronaphthyridine. The contents of the 5 vials were transferred into a separatory funnel and partitioned between 300 mL each EtOAc and brine, and the aqueous layer extracted twice more with EtOAc. The combined organic extracts were washed with brine (3×), dried over anhydrous $MgSO_4$, filtered and evaporated. To purify the crude product, it was first recrystallized from 250 mL 1:1 MeCN/EtOH. The yellow crystals were washed with MeOH and dried under vacuum, and then purified further by flash chromatography over silica gel (7-8% MeOH in $CH_2Cl_2$). The filtrate from the recrystallization was evaporated and the residue purified by flash chromatography over silica gel (7% MeOH in $CH_2Cl_2$) and recrystallization from 100 mL 1:1 MeCN/EtOH. The two lots of purified product were combined, pulverized with the flattened end of a glass rod, and dried in a vacuum oven for 6 days, giving pure product as a bright yellow powder (1.17 g, 24% yield): $^1$H NMR (400 MHz, DMSO-$D_6$) δ 4.58 (d, J=6.3 Hz, 2 H) 7.10 (s, 1 H) 7.26-7.39 (m, 2 H) 7.46 (t, J=9.0 Hz, 1 H) 7.54 (t, J=6.3 Hz, 1 H) 7.59 (dd, J=6.6, 2.8 Hz, 1H) 7.75 (dt, J=7.8, 1.6 Hz, 1 H) 8.29 (s, 1 H) 8.44 (dd, J=4.7, 1.6 Hz, 1 H) 8.60 (d, J=1.8 Hz, 1 H) 8.87 (s, 1 H) 9.67 (s, 1 H); HRMS (ESI+) calcd for $C_{21}H_{15}ClFN_6$ (MH+) 405.1026, found 405.1030. Anal. Calcd for $C_{21}H_{14}ClFN_6$: C, 62.30; H, 3.49; N, 20.76. Found: C, 62.04; H, 3.52; N, 20.48.

Example 2

6-(2-morpholinoethylamino)-4-(3-phenoxyphenylamino)-1,7-naphthyridine-3-carbonitrile In a 100 mL round-bottomed flask fitted with a condenser, 4-chloro-6-fluoro-1,7-naphthyridine-3-carbonitrile (0.250 g, 1.20 mmol) and 3-phenoxyaniline (0.245 g, 1.32 mmol) were taken up in 20 mL 2-ethoxyethanol and heated at reflux for 1 hour, until TLC analysis (20% EtOAc in hexanes) showed complete disappearance of the 4-chloronaphthyridine. After cooling to room temperature, the reaction mixture was partitioned between 40 mL each EtOAc and 5% $Na_2CO_3$. The aqueous layer was extracted twice more with EtOAc, and the combined organic layers washed three times with brine, dried over anhydrous $MgSO_4$, filtered, and evaporated to give 6-fluoro-4-(3-phenoxyphenylamino)-1,7-naphthyridine-3-carbonitrile as a brown oil of sufficient purity to be used directly in the next step: $^1$H NMR (400 MHz, DMSO-$D_6$) δ 6.94-7.18 (m, 6 H) 7.33-7.51 (m, 3 H) 8.15 (s, 1 H) 8.68 (s, 1 H) 9.05 (s, 1 H) 10.12 (s, 1 H).

The product of the first step (0.14 g, 0.40 mmol, assuming 100% yield of step 1) was taken up in a microwave vial in 3.4 mL THF, with 4-(2-aminoethyl)morpholine (1.1 mL, 1.0 g, 8.0 mmol). The sealed vial was heated in a microwave reactor at 150° C. for 80 minutes, until TLC analysis showed complete disappearance of the starting material. The contents of the vial were then partitioned between 20 mL each EtOAc and brine. The aqueous layer was extracted twice more with EtOAc, and the combined organic extracts washed with brine, dried over anhydrous $MgSO_4$, filtered and evaporated. The crude product was purified by flash chromatography over silica gel (5% MeOH in $CH_2Cl_2$) and lyophilized to give pure product as a fluffy, bright yellow solid (50 mg, 27% yield of 2 steps): $^1$H NMR (400 MHz, DMSO-$D_6$) δ 2.44 (br s, 4 H) 2.57 (t, J=6.3 Hz, 2 H) 3.34-3.43 (m, 2 H) 3.49-3.64 (m, 4 H) 6.64 (t, J=5.8 Hz, 1 H) 6.90 (dd, J=3.8, 1.5 Hz, 2 H) 7.00 (s, 1 H) 7.03-7.11 (m, 3 H) 7.14 (t, J=7.5 Hz, 1 H) 7.33-7.47 (m, 3 H) 8.28 (s, 1 H) 8.84 (s, 1 H) 9.64 (s, 1 H); HRMS (ESI+) calcd for $C_{27}H_{27}N_6O_2$ (MH+) 467.2190, found 467.2188.

Example 3

4-(3-chlorophenylamino)-6-(2-morpholinoethy-lamino)-1,7-naphthyridine-3-carbonitrile Following the procedure described above in Example 2, 4-chloro-6-fluoro-1,7-naphthyridine-3-carbonitrile (0.250 g, 1.20 mmol) was reacted with 3-chloroaniline (0.17 g, 1.3 mmol) to give 4-(3-chlorophenylamino)-6-fluoro-1,7-naphthyridine-3-carbonitrile as a golden-brown oil which crystallized slowly upon standing, and was of sufficient purity to be used directly in the next step: $^1$H NMR (400 MHz, DMSO-$D_6$) δ 7.29-7.41 (m, 2 H) 7.43-7.51 (m, 2 H) 8.16 (s, 1 H) 8.72 (s, 1 H) 9.09 (s, 1 H) 10.14 (s, 1 H).

The product of the first step (0.119 g, 0.400 mmol, assuming 100% yield of step 1) was reacted with 4-(2-aminoethyl)morpholine (1.1 mL, 1.0 g, 8.0 mmol), and the crude product purified by flash chromatography over silica gel (7% MeOH in $CH_2Cl_2$) and lyophilized to give a fluffy, bright yellow solid (46 mg, 28% yield of 2 steps): $^1$H NMR (400 MHz, DMSO-$D_6$) δ 2.45 (br s, 4 H) 2.57 (t, J=6.8 Hz, 2 H) 3.38 (q, J=6.4 Hz, 2 H) 3.50-3.65 (m, 4 H) 6.68 (t, J=5.4 Hz, 1 H) 6.99 (s, 1 H) 7.25 (ddd, J=14.9, 8.0, 1.4 Hz, 2 H) 7.34 (t, J=1.9 Hz, 1 H) 7.42 (t, J=8.1 Hz, 1 H) 8.32 (s, 1 H) 8.87 (s, 1 H) 9.65 (s, 1 H); HRMS (ESI+) calcd for $C_{21}H_{22}ClN_6O$ (MH+) 409.1538, found 409.1537.

Example 4

4-(4-fluorophenylamino)-6-(2-morpholinoethy-lamino)-1,7-naphthryidine-3-carbonitrile Following the procedure described above in Example 2, 4-chloro-6-fluoro-1,7-naphthyridine-3-carbonitrile (0.250 g, 1.20 mmol) was reacted with 4-fluoroaniline (0.133 g, 1.32 mmol) to give 4-(4-fluorophenylamino)-6-fluoro-1,7-naphthyridine-3-carbonitrile as a golden-brown oil which crystallized slowly upon standing, and was of sufficient purity to be used directly in the next step: $^1$H NMR (400 MHz, DMSO-D$_6$) □ 7.27-7.36 (m, 2 H) 7.41-7.49 (m, 2 H) 8.19 (s, 1 H) 8.63 (s, 1 H) 9.05 (s, 1 H) 10.09 (s, 1 H).

The product of the first step (0.113 g, 0.400 mmol, assuming 100% yield of step 1) was reacted with 4-(2-aminoethyl)morpholine (1.1 mL, 1.0 g, 8.0 mmol), and the crude product purified by flash chromatography over silica gel (7% MeOH in CH$_2$Cl$_2$) and lyophilized to give a fluffy, bright yellow solid (41 mg, 26% yield of 2 steps): $^1$H NMR (400 MHz, DMSO-D$_6$) □ 2.45 (br s, 4 H) 2.58 (br s, 2 H) 3.38 (q, J=6.4 Hz, 2 H) 3.52-3.64 (m, 4 H) 6.60 (t, J=6.2 Hz, 1 H) 7.06 (s, 1 H) 7.27 (t, J=8.8 Hz, 2 H) 7.33-7.43 (m, 2 H) 8.22 (s, 1 H) 8.82 (s, 1 H) 9.60 (s, 1 H); HRMS (ESI+) calcd for C$_{21}$H$_{22}$FN$_6$O (MH+) 393.1834, found 393.1833.

Example 5

4-(4-bromophenylamino)-6-(2-morpholinoethylamino)-1,7-naphthyridine-3-carbonitrile Following the procedure described above in Example 2, 4-chloro-6-fluoro-1,7-naphthyridine-3-carbonitrile (0.250 g, 1.20 mmol) was reacted with 4-bromoaniline (0.227 g, 1.32 mmol) to give 4-(4-bromophenylamino)-6-fluoro-1,7-naphthyridine-3-carbonitrile as a golden-brown powder, which was of sufficient purity to be used directly in the next step: $^1$H NMR (400 MHz, DMSO-D$_6$) δ 7.28-7.40 (m, 2 H) 7.64 (m, 2 H) 8.17 (s, 1 H) 8.69 (s, 1 H) 9.07 (s, 1 H) 10.10 (s, 1 H).

The product of the first step (0.137 g, 0.400 mmol, assuming 100% yield of step 1) was reacted with 4-(2-aminoethyl)morpholine (1.1 mL, 1.0 g, 8.0 mmol), and the crude product purified by flash chromatography over silica gel (7% MeOH in CH$_2$Cl$_2$) and lyophilized to give a fluffy, bright yellow solid (61 mg, 34% yield of 2 steps): $^1$H NMR (400 MHz, DMSO-D$_6$) δ 2.44 (br s, 4 H) 2.56 (t, J=6.7 Hz, 2 H) 3.37 (q, J=6.5 Hz, 2 H) 3.53-3.63 (m, 4 H) 6.66 (t, J=5.7 Hz, 1 H) 7.00 (s, 1 H) 7.24 (d, J=8.6 Hz, 2 H) 7.58 (d, J=8.8 Hz, 2 H) 8.29 (s, 1 H) 8.85 (s, 1 H) 9.62 (s, 1 H); HRMS (ESI+) calcd for C$_{21}$H$_{22}$BrN$_6$O (MH+) 453.1033, found 453.1035.

Example 6

4-(4-benzylphenylamino)-6-fluoro-1,7-naphthyridine-3-carbonitrile

Following the procedure described above in Example 2, 4-chloro-6-fluoro-1,7-naphthyridine-3-carbonitrile (0.750 g, 3.61 mmol) was reacted with 4-benzylaniline (0.728 g, 3.97 mmol) in 60 mL DME. When TLC analysis (20% EtOAc in hexanes) showed that the 4-chloronaphthyridine had been completely consumed, the reaction was allowed to cool to room temperature and worked up. DME was removed under reduced pressure, and the residue partitioned between 100 mL each 5% Na$_2$CO$_3$ and EtOAc. The aqueous layer was extracted twice more with EtOAc, and the combined organic layers washed with brine, dried over anhydrous MgSO$_4$, filtered, and evaporated. The crude product was then dissolved in a minimum of EtOAc, and hexanes were added slowly, with vigorous stirring, until product precipitated. The precipitate was collected by suction filtration, washing three times with hexanes, and dried under vacuum to give pure product as a mustard-yellow powder (0.896 g, 70% yield): $^1$H NMR (400 MHz, DMSO-D$_6$) δ 4.00 (s, 2 H) 7.14-7.24 (m, 3 H) 7.24-7.29 (m, 2 H) 7.29 (s, 4 H) 8.17 (s, 1 H) 8.62 (s, 1 H) 9.03 (s, 1 H) 10.03 (s, 1 H); HRMS (ESI+) calcd for C$_{22}$H$_{16}$FN$_4$ (MH+) 355.1354, found 355.1361. Anal. Calcd for C$_{22}$H$_{15}$FN$_4$: C, 74.56; H, 4.27; N, 15.81. Found: C, 74.32; H, 4.29; N, 15.57.

Example 7

4-(4-benzylphenylamino)-6-(2-morpholinoethylamino)-1,7-naphthyridine-3-carbonitrile Following the procedure described above in Example 1, 4-(4-benzylphenylamino)-6-fluoro-1,7-naphthyridine-3-carbonitrile (0.675 g, 1.90 mmol) was reacted with 4-(2-aminoethyl)morpholine (5.0 mL, 5.0 g, 38 mmol). This process was repeated with three additional aliquots of 4-(4-benzylphenylamino)-6-fluoro-1,7-naphthyridine-3-carbonitrile (0.62 g, 0.62 g, 0.30 g). The contents of all four tubes were worked up together, and the crude product purified by flash chromatography over silica gel (5-6% MeOH in CH$_2$Cl$_2$) to give pure product as bright yellow crystals (1.17 g, 40% yield): $^1$H NMR (400 MHz, DMSO-D$_6$) δ 2.43 (br s, 4 H) 2.56 (t, J=6.7 Hz, 2 H) 3.31-3.39 (m, 2 H) 3.50-3.66 (m, 4 H) 3.99 (s, 2 H) 6.58 (t, J=4.9 Hz, 1 H) 7.04 (s, 1 H) 7.13-7.35 (m, 9 H) 8.22 (s, 1 H) 8.82 (s, 1 H) 9.56 (s, 1 H); HRMS (ESI+) calcd for C$_{28}$H$_{29}$N$_6$O (MH+) 465.2398, found 465.2396.

Example 8

4-(4-chlorophenylamino)-6-(2-morpholinoethylamino)-1,7-naphthyridine-3-carbonitrile Following the procedure described above in Example 2, 4-chloro-6-fluoro-1,7-naphthyridine-3-carbonitrile (0.250 g, 1.20 mmol) was reacted with 4-chloroaniline (0.168 g, 1.32 mmol) to give 4-(4-chlorophenylamino)-6-fluoro-1,7-naphthyridine-3-carbonitrile as a crystalline yellow solid, which was of sufficient purity to be used directly in the next step: $^1$H NMR (400 MHz, DMSO-D$_6$) δ 7.41 (d, J=8.6 Hz, 2 H) 7.47-7.58 (m, 2 H) 8.18 (s, 1 H) 8.69 (s, 1 H) 9.07 (s, 1 H) 10.11 (s, 1 H).

The product of the first step (0.179 g, 0.600 mmol) was reacted with 4-(2-aminoethyl)morpholine (1.6 mL, 1.6 g, 12 mmol), the THF removed under reduced pressure, and the crude product purified by flash chromatography over silica gel (7% MeOH in CH$_2$Cl$_2$) and lyophilized to give a fluffy, bright yellow solid (105 mg, 43% yield of 2 steps): $^1$H NMR (400 MHz, DMSO-D$_6$) δ 2.43 (br s, 4 H) 2.56 (t, J=6.2 Hz, 2H) 3.37 (q, J=6.6 Hz, 2 H) 3.49-3.64 (m, 4 H) 6.65 (t, J5.8 Hz, 1 H) 7.01 (s, 1 H) 7.31 (d, J=8.6 Hz, 2 H) 7.46 (d, J=8.8 Hz, 2 H) 8.28 (s, 1 H) 8.85 (s, 1 H) 9.63 (s, 1 H);

HRMS (ESI+) calcd for C$_{21}$H$_{22}$ClN$_6$O (MH+) 409.1538. found 409.1542.

Example 9

4-(4-fluorophenylamino)-6-(pyridin-3-ylmethylamino)-1,7-naphthyridine-3-carbonitrile Following the procedure described above in Example 2, 6-fluoro-4-(4-fluorophenylamino)-1,7-naphthyridine-3-carbonitrile (0.113 g, 0.400 mmol) was reacted with 3-(aminomethyl)pyridine (0.82 mL, 0.87 g, 8.0 mmol). The crude product was purified first by flash chromatography over silica gel (8% MeOH in CH$_2$Cl$_2$), then by the Chemical Technologies group (preparative HPLC), then lyophilized, to give a fluffy, bright yellow solid (9.7 mg, 6.6% yield): $^1$H NMR (400

MHz, DMSO-$D_6$) δ 4.57 (d, J=6.3 Hz, 2 H) 7.16 (s, 1 H) 7.25 (t, J=8.7 Hz, 2 H) 7.30-7.43 (m, 3 H) 7.49 (t, J=6.2 Hz, 1 H) 7.76 (d, J=7.3 Hz, 1 H) 8.22 (s, 1 H) 8.44 (d, J=4.8 Hz, 1 H) 8.61 (d, J=1.3 Hz, 1 H) 8.84 (s, 1 H) 9.64 (s, 1 H); HRMS (ESI+) calcd for $C_{21}H_{16}FN_6$ (MH+) 371.1415, found 371.1423.

Example 10

6-(2-morpholinoethylamino)-4-(4-(phenylamino) phenylamino)-1,7-naphthyridine-3-carbonitrile Following the procedure described above in Example 2, 4-chloro-6-fluoro-1,7-naphthyridine-3-carbonitrile (0.250 g, 1.20 mmol) was reacted with $N^1$-phenylbenzene-1,4-diamine (0.243 g, 1.32 mmol) to give 6-fluoro-4-(4-(phenylamino) phenylamino)-1,7-naphthyridine-3-carbonitrile as a dark brown solid, which was of sufficient purity to be used directly in the next step: $^1$H NMR (400 MHz, DMSO-$D_6$) δ 6.86 (tt, J=7.3, 1.0 Hz, 1 H) 7.07-7.17 (m, 4 H) 7.21-7.32 (m, 4 H) 8.21 (s, 1 H) 8.37 (s, 1 H) 8.58 (s, 1 H) 9.02 (s, 1 H) 9.99 (s, 1 H).

The product of the first step (0.213 g, 0.600 mmol) was reacted with 4-(2-aminoethyl)morpholine (1.56 g, 12 mmol), and the crude product purified by flash chromatography over silica gel (7% MeOH in $CH_2Cl_2$) and lyophilized to give a fluffy, golden yellow solid (37 mg, 13% yield of 2 steps): $^1$H NMR (400 MHz, DMSO-$D_6$) δ 2.45 (br s, 4 H) 2.58 (t, J=6.4 Hz, 2 H) 3.37 (q, J=6.7 Hz, 2 H) 3.55-3.64 (m, 4 H) 6.53 (t, J=5.4 Hz, 1 H) 6.85 (t, J=7.2 Hz, 1 H) 7.05-7.17 (m, 5 H) 7.17-7.31 (m, 4 H) 8.17 (s, 1 H) 8.31 (s, 1 H) 8.79 (s, 1 H) 9.53 (s, 1 H); HRMS (ESI+) calcd for $C_{27}H_{28}N_7O$ (MH+) 466.23500, found 466.23501.

Example 11

6-(2-morpholinoethylamino)-4-(4-(phenylthio)phenylamino)-1,7-naphthyridine-3-carbonitrile Following the procedure described above in Example 2, 4-chloro-6-fluoro-1,7-naphthyridine-3-carbonitrile (0.250 g, 1.20 mmol) was reacted with 4-(phenylthio)aniline (0.266 g, 1.32 mmol) in 20 mL 2-ethoxyethanol. Work-up of the reaction mixture gave 6-fluoro-4-(4-(phenylthio)phenylamino)-1,7-naphthyridine-3-carbonitrile as a dark red oil which crystallized upon standing, and was of sufficient purity to be used directly in the next step: $^1$H NMR (400 MHz, DMSO-$D_6$) δ 7.27-7.32 (m, 3 H) 7.33-7.43 (m, 4 H) 7.43-7.48 (m, 2 H) 8.17 (s, 1 H) 8.69 (s, 1 H) 9.08 (s, 1H) 10.16 (s, 1 H).

The product of the first step (0.224 g, 0.600 mmol) was reacted with 4-(2-aminoethyl)morpholine (1.56 g, 12.0 mmol), and the crude product purified by flash chromatography over silica gel (5% MeOH in $CH_2Cl_2$) and lyophilized to give pure product as a bright yellow powder (0.114 g, 39% yield over two steps): $^1$H NMR (400 MHz, DMSO-$D_6$) δ 2.44 (br s, 4 H) 2.56 (br s, 2 H) 3.37 (q, J=6.0 Hz, 2 H) 3.48-3.67 (m, 4 H) 6.66 (t, J=5.7 Hz, 1 H) 7.01 (s, 1 H) 7.19-7.28 (m, 3 H) 7.28-7.39 (m, 4 H) 7.39-7.50 (m, 2 H) 8.30 (s, 1 H) 8.86 (s, 1 H) 9.69 (s, 1 H); HRMS (ESI+) calcd for $C_{27}H_{17}N_6OS$ (MH+) 483.1962, found 483.1957.

Example 12

4-(3-chlorophenylamino)-6-(pyridin-3-ylmethylamino)-1,7-naphthyridine-3-carbonitrile Following the procedure described above in Example 2, 4-(3-chlorophenylamino)-6-fluoro-1,7-naphthyridine-3-carbonitrile (0.119 g, 0.400 mmol) was reacted with 3-(aminomethyl)pyridine (0.82 mL, 0.87 g, 8.0 mmol) in 3.4 mL THF. The crude product was purified first by flash chromatography over silica gel (8% MeOH in $CH_2Cl_2$), then a second time by preparative HPLC, and finally lyophilized to give pure product as a fluffy, bright yellow solid (9.5 mg, 6.1% yield): $^1$H NMR (400 MHz, DMSO-$D_6$) δ 4.56 (d, J=6.3 Hz, 2 H) 7.10 (s, 1 H) 7.21 (dd, J=18.6, 8.0 Hz, 2 H) 7.28-7.36 (m, 2 H) 7.39 (t, J=8.1 Hz, 1 H) 7.52 (t, J=5.7 Hz, 1 H) 7.70-7.79 (m, 1 H) 8.30 (s, 1 H) 8.43 (dd, J=4.9, 1.4 Hz, 1 H) 8.59 (d, J=2.0 Hz, 1 H) 8.86 (s, 1 H) 9.69 (br s, 1 H); HRMS (ESI+) calcd for $C_{21}H_{16}ClN_6$ (MH+) 387.1120, found 387.1122.

Example 13

4-(3,4-difluorophenylamino)-6-(2-morpholinoethylamino)-1,7-naphthryidine-3-carbonitrile Following the procedure described above in Example 1, 4-chloro-6-fluoro-1,7-naphthyridine-3-carbonitrile (0.250 g, 1.20 mmol) was reacted with 3,4-difluoroaniline (0.13 mL, 0.17 g, 1.3 mmol) in 5 mL 2-ethoxyethanol. Work-up of the reaction gave 6-fluoro-4-(3,4-difluorophenylamino)-1,7-naphthyridine-3-carbonitrile of sufficient purity to be used directly in the next step: $^1$H NMR (400 MHz, DMSO-$D_6$) δ 7.18-7.36 (m, 1 H) 7.43-7.65 (m, 2 H) 8.17 (s, 1 H) 8.69 (s, 1 H) 9.08 (s, 1 H) 10.16 (s, 1 H).

Following the procedure described above in Example 2, the above product (0.180 g, 0.600 mmol, assuming 100% yield) was reacted with 4-(2-aminoethyl)morpholine (1.56 g, 12.0 mmol). The crude product was purified by flash chromatography over silica gel (7% MeOH in $CH_2Cl_2$) and lyophilized to give a fluffy, bright yellow solid (58 mg, 24% yield of 2 steps): $^1$H NMR (400 MHz, DMSO-$D_6$) δ 2.45 (br s, 4 H) 2.57 (t, J=6.4 Hz, 2 H) 3.34-3.42 (m, 2 H) 3.51-3.64 (m, 4 H) 6.66 (t, J=5.7 Hz, 1 H) 7.02 (s, 1 H) 7.13-7.24 (m, 1 H) 7.43-7.58 (m, 2 H) 8.28 (s, 1 H) 8.85 (s, 1 H) 9.68 (s, 1 H); HRMS (ESI+) calcd for $C_{21}H_{21}F_2N_6O$ (MH+) 411.1740, found 411.1737.

Example 14

4-(4-benzylphenylamino)-6-(pyridin-3-ylmethylamino)-1,7-naphthryidine-3-carbonitrile Following the procedure described above in Example 2, 4-(4-benzylphenylamino)-6-fluoro-1,7-naphthyridine-3-carbonitrile (0.213 g, 0.600 mmol) was reacted with 3-(aminomethyl)pyridine (1.22 mL, 1.30 g, 12.0 mmol) in 3.4 mL THF. The crude product was purified first by flash chromatography over silica gel (5% MeOH in $CH_2Cl_2$), then by preparative HPLC, and finally lyophilized to give pure product as a fluffy, bright yellow solid (23 mg, 8.7% yield): $^1$H NMR (400 MHz, DMSO-$D_6$) δ 3.99 (s, 2 H) 4.53 (d, J=5.8 Hz, 2 H) 7.12 (s, 1 H) 7.15-7.37 (m, 10 H) 7.48 (t, J=6.3 Hz, 1 H) 7.74 (d, J=8.1 Hz, 1 H) 8.23 (s, 1 H) 8.43 (d, J=3.5 Hz, 1 H) 8.58 (s, 1 H) 8.83 (s, 1 H) 9.58 (s, 1 H); HRMS (ESI+) calcd for $C_{28}H_{23}N_6$ (MH+) 443.1979, found 443.1982.

Example 15

4-(3-phenoxyphenylamino)-6-(pyridin-3-ylmethylamino)-1,7-naphthyridine-3-carbonitrile Following the procedure described above in Example 2, 6-fluoro-4-(3-phenoxyphenylamino)-1,7-naphthyridine-3-carbonitrile (0.14 g, 0.40 mmol) was reacted with 3-(aminomethyl)pyridine (0.82 mL, 0.87 g, 8.0 mmol). Crude product was purified first by flash chromatography over silica gel (7% MeOH in CH$_2$Cl$_2$), then by preparative HPLC, and finally lyophilized to give a fluffy, bright yellow solid (17 mg, 9.6% yield): $^1$H NMR (400 MHz, DMSO-D$_6$) δ 4.56 (d, J=6.6 Hz, 2 H) 6.86 (s, 2 H) 7.00-7.16 (m, 5 H) 7.23-7.44 (m, 4 H) 7.44-7.58 (m, 1 H) 7.74 (d, J6.8 Hz, 1 H) 8.26 (s, 1 H) 8.43 (s, 1 H) 8.59 (s, 1 H) 8.82 (s, 1 H) 9.70 (br s, 1 H); HRMS (ESI+) calcd for C$_{27}$H$_{21}$N$_6$O (MH+) 445.1772, found 445.1774.

Example 16

4-(4-chlorophenylamino)-6-(pyridin-3-ylmethylamino)-1,7-naphthyridine-3-carbonitrile Following the procedure described above in Example 2,4-(4-chlorophenylamino)-6-fluoro-1,7-naphthyridine-3-carbonitrile (0.179 g, 0.600 mmol) was reacted with 3-(aminomethyl)pyridine (1.22 mL, 1.30 g, 12.0 mmol) in THF. The crude product was purified first by flash chromatography over silica gel (5% MeOH in CH$_2$Cl$_2$), then by preparative HPLC, and finally lyophilized to give a fluffy, bright yellow solid (26 mg, 11% yield): $^1$H NMR (400 MHz, DMSO-D$_6$) δ 4.57 (d, J=6.3 Hz, 2 H) 7.12 (s, 1 H) 7.29 (d, J=8.8 Hz, 2 H) 7.33 (dd, J=7.7, 4.9 Hz, 1 H) 7.45 (d, J=8.6 Hz, 2 H) 7.52 (t, J=6.1 Hz, 1 H) 7.75 (d, J=8.1 Hz, 1 H) 8.29 (s, 1 H) 8.43 (d, J=4.3 Hz, 1 H) 8.60 (s, 1 H) 8.86 (s, 1 H) 9.67 (br s, 1 H); HRMS (ESI+) calcd for C$_{21}$H$_{16}$ClN$_6$ (MH+) 387.1120, found 387.1125.

Example 17

4-(4-bromophenylamino)-6-(pyridin-3-ylmethylamino)-1,7-naphthyridine-3-carbonitrile Following the procedure described above in Example 2,4-(4-bromophenylamino)-6-fluoro-1,7-naphthyridine-3-carbonitrile (0.161 g, 0.470 mmol) was reacted with 3-(aminomethyl)pyridine (0.96 mL, 1.0 g, 9.4 mmol). The crude product was purified first by flash chromatography over silica gel (8% MeOH in CH$_2$Cl$_2$), then by preparative HPLC, and finally lyophilized to give a fluffy, bright yellow solid (34 mg, 17% yield): $^1$H NMR (400 MHz, DMSO-D$_6$) δ 4.57 (d, J=6.1 Hz, 2 H) 7.10 (s, 1 H) 7.22 (d, J=8.6 Hz, 2 H) 7.33 (dd, J=7.7, 4.7 Hz, 1 H) 7.52 (t, J=5.9 Hz, 1 H) 7.56 (d, J=8.8 Hz, 2 H) 7.74 (dt, J=7.8, 1.9 Hz, 1 H) 8.29 (s, 1 H) 8.43 (dd, J=4.8, 1.5 Hz, 1 H) 8.59 (d, J=1.8 Hz, 1 H) 8.86 (s, 1 H) 9.63 (s, 1 H); HRMS (ESI+) calcd for C$_{21}$H$_{16}$BrN$_6$ (MH+) 431.0615, found 431.0620.

Example 18

4-(4-(phenylamino)phenylamino)-6-(pyridin-3-ylmethylamino)-1,7-naphthyridine-3-carbonitrile Following the procedure described above in Example 2,6-fluoro-4-(4-(phenylamino)phenylamino)-1,7-naphthyridine-3-carbonitrile (0.213 g, 0.600 mmol) was reacted with 3-(aminomethyl)pyridine (1.22 mL, 1.30 g, 12.0 mmol). The crude product was purified first by flash chromatography over silica gel (5-7% MeOH in CH$_2$Cl$_2$, followed by 100% EtOAc), then by preparative HPLC, and finally lyophilized to give a golden brown powder (23 mg, 8.4% yield): $^1$H NMR (400 MHz, DMSO-D$_6$) δ 4.57 (d, J=6.6 Hz, 2 H) 6.84 (t, J=7.5 Hz, 1 H) 7.10 (dd, J=8.2, 3.9 Hz, 4 H) 7.15-7.22 (m, 3 H) 7.25 (t, J=7.8 Hz, 2 H) 7.35 (dd, J=7.7, 4.9 Hz, 1 H) 7.45 (t, J=6.6 Hz, 1 H) 7.77 (d, J=7.8 Hz, 1 H) 8.18 (s, 1 H) 8.32 (s, 1 H) 8.44 (dd, J=4.7, 0.9 Hz, 1 H) 8.62 (s, 1 H) 8.81 (s, 1 H) 9.54 (s, 1 H); HRMS (ESI+) calcd for C$_{28}$H$_{22}$N$_7$ (MH+) 444.1931, found 444.1936.

Example 19

4-(4-(phenylthio)phenylamino)-6-(pyridin-3-ylmethylamino)-1,7-naphthyridine-3-carbonitrile Following the procedure described above in Example 2,6-fluoro-4-(4-(phenylthio)phenylamino)-1,7-naphthyridine-3-carbonitrile (0.224 g, 0.600 mmol) was reacted with 3-(aminomethyl)pyridine (1.22 mL, 1.30 g, 12.0 mmol) in 3.4 mL THF. The crude product was purified first by flash chromatography over silica gel (5% MeOH in CH$_2$Cl$_2$), then by preparative HPLC, and finally lyophilized. Pure product was obtained as a bright yellow powder (37 mg, 13% yield): $^1$H NMR (400 MHz, DMSO-D$_6$) δ 4.57 (d, J=6.3 Hz, 2 H) 7.11 (s, 1 H) 7.21-7.37 (m, 8 H) 7.42 (d, J=8.6 Hz, 2 H) 7.53 (t, J=6.4 Hz, 1 H) 7.75 (d, J=7.8 Hz, 1 H) 8.30 (s, 1 H) 8.44 (d, J=3.8 Hz, 1 H) 8.59 (d, J=1.5 Hz, 1 H) 8.87 (s, 1 H) 9.72 (br s, 1 H); HRMS (ESI+) calcd for C$_{27}$H$_{21}$N$_6$S (MH+) 461.1543, found 461.1548.

Example 20

4-(3,4-difluorophenylamino)-6-(pyridin-3-ylmethylamino)-1,7-naphthyridine-3-carbonitrile Following the procedure described above in Example 2,6-fluoro-4-(3,4-difluorophenylamino)-1,7-naphthyridine-3-carbonitrile (0.180 g, 0.600 mmol) was reacted with 3-(aminomethyl)pyridine (0.92 mL, 0.97 g, 9.0 mmol) in 3.4 mL THF. The crude product was purified first by flash chromatography over silica gel (7% MeOH in CH$_2$Cl$_2$), then preparative HPLC, then lyophilized to give pure product as a fluffy, bright yellow solid: $^1$H NMR (400 MHz, DMSO-D$_6$) δ 4.57 (d, J=6.6 Hz, 2 H) 7.13 (s, 2 H) 7.33 (dd, J=7.8, 5.1 Hz, 1 H) 7.37-7.55 (m, 3 H) 7.75 (d, J=8.1 Hz, 1 H) 8.26 (s, 1 H) 8.43 (d, J=5.3 Hz, 1 H) 8.59 (s, 1 H) 8.84 (s, 1 H) 9.76 (br s, 1 H); HRMS (ESI+) calcd for C$_{21}$H$_{15}$F$_2$N$_6$ (MH+) 389.1321, found 389.1328.

Example 21

4-(4-benzylphenylamino)-6-(3-(dimethylamino)propylamino)-1,7-naphthyridine-3-carbonitrile Following the procedure described above in Example 2,4-(4-benzylphenylamino)-6-fluoro-1,7-naphthyridine-3-carbonitrile (0.150 g, 0.423 mmol) was reacted with 3-(dimethylamino)propylamine (1.1 mL, 0.86 g, 8.5 mmol) in 3.5 mL THF. The crude product obtained was purified by flash chromatography over silica gel (5% MeOH in CH$_2$Cl$_2$+2% Et$_3$N) and lyophilized to give pure product as a fluffy bright yellow solid (96 mg, 52% yield): $^1$H NMR (400 MHz, DMSO-D$_6$) δ 1.74 (quin., 2 H) 2.15 (s, 6 H) 2.34 (t, J=7.0 Hz, 2 H) 3.23 (q, J=6.5 Hz, 2 H) 3.99 (s, 2 H) 6.85 (t, J=5.6 Hz, 1 H) 6.97 (s, 1 H) 7.15-7.32 (m, 9 H) 8.21 (s, 1 H) 8.80 (s, 1 H) 9.57 (s, 1 H); HRMS (ESI+) calcd for C$_{27}$H$_{29}$N$_6$ (MH+) 420.1779, found 420.1775.

Example 22

4-(4-benzylphenylamino)-6-(3-(4-methylpiperazin-1-yl)propylamino)-1,7-naphthyridine-3-carbonitrile Following the procedure described above in Example 2,4-(4-benzylphenylamino)-6-fluoro-1,7-naphthyridine-3-carbonitrile (0.150 g, 0.423 mmol) was reacted with 3-(4-methylpiperazin-1-yl)-propan-1-amine (1.33 g, 8.46 mmol) in 3.5 mL THF. The crude product was purified by flash chromatography over silica gel (5% MeOH in $CH_2Cl_2$+2% $Et_3N$) and lyophilized to give pure product as a fluffy bright yellow solid (0.107 g, 52% yield): $^1H$ NMR (400 MHz, DMSO-$D_6$) δ 1.66-1.81 (m, 2 H) 2.26 (br s, 3 H) 2.43 (br s, 8 H) 3.19-3.28 (m, 2 H) 3.32 (br s, 2 H) 3.99 (s, 2 H) 6.85 (t, J=5.6 Hz, 1 H) 6.99 (s, 1 H) 7.15-7.33 (m, 9 H) 8.21 (s, 1 H) 8.81 (s, 1 H) 9.59 (s, 1 H); HRMS (ESI+) calcd for $C_{30}H_{34}N_7$ (MH+) 492.2870, found 492.2861.

Example 23

4-(4-benzylphenylamino)-6-(2-(dimethylamino)ethylamino)-1,7-naphthyridine-3-carbonitrile Following the procedure described above in Example 2, 4-(4-benzylphenylamino)-6-fluoro-1,7-naphthyridine-3-carbonitrile (0.150 g, 0.423 mmol) was reacted with N,N-dimethylethylenediamine (0.93 mL, 0.75 g, 8.5 mmol) in 3.5 mL THF. The crude product was purified by flash chromatography over silica gel (3% MeOH in $CH_2Cl_2$+2% $Et_3N$) and lyophilized to give pure product as a fluffy bright yellow solid (85 mg, 47% yield): $^1H$ NMR (400 MHz, DMSO-$D_6$) δ 2.21 (s, 6 H) 3.26-3.41 (m, 4 H) 3.99 (s, 2 H) 6.53 (t, J=5.6 Hz, 1 H) 7.03 (s, 1 H) 7.14-7.33 (m, 9 H) 8.22 (s, 1 H) 8.81 (s, 1 H) 9.56 (s, 1 H); HRMS (ESI+) calcd for $C_{26}H_{27}N_6$ (MH+) 423.2292, found 423.2288.

Example 24

4-(3-fluorophenylamino)-6-(2-morpholinoethylamino)-1,7-naphthyridine-3-carbonitrile Following the procedure described above in Example 13, 4-chloro-6-fluoro-1,7-naphthyridine-3-carbonitrile (0.300 g, 1.45 mmol) was reacted with 3-fluoroaniline (0.15 mL, 0.18 g, 1.6 mmol). The crude product was purified by flash chromatography over silica gel (10% EtOAc in $CH_2Cl_2$) to give pure 6-fluoro-4-(3-fluorophenylamino)-1,7-naphthyridine-3-carbonitrile (0.185 g, 45% yield): $^1H$ NMR (400 MHz, DMSO-$D_6$) δ 7.16 (td, J=8.5, 2.7 Hz, 1 H) 7.22 (ddd, J 8.0, 2.0, 0.9 Hz, 1 H) 7.27 (dt, J=10.2, 2.2 Hz, 1 H) 7.43-7.53 (m, 1 H) 8.17 (s, 1 H) 8.72 (s, 1 H) 9.10 (s, 1 H) 10.16 (s, 1 H).

The product of the first step (92.5 mg, 0.328 mmol) was reacted with 4-(2-aminoethyl)morpholine (0.853 g, 6.55 mmol) in 4.3 mL THF. The crude product was purified by flash chromatography over silica gel (7% MeOH in $CH_2Cl_2$) and lyophilized to give a fluffy, bright yellow solid: $^1H$ NMR (400 MHz, DMSO-$D_6$) δ 2.43 (br s, 4 H) 2.56 (t, J=6.19 Hz, 2 H) 3.37 (q, J=6.2 Hz, 2 H) 3.53-3.63 (m, 4 H) 6.67 (t, J=5.7 Hz, 1 H) 7.00 (s, 1 H) 7.09-7.16 (m, 2 H) 7.38-7.48 (m, 1 H) 8.32 (s, 1 H) 8.87 (s, 1 H) 9.67 (s, 1 H); HRMS (ESI+) calcd for $C_{21}H_{22}FN_6O$ (MH+) 393.1834, found 393.1825.

Example 25

4-(4-benzylphenylamino)-6-(2-(piperazin-1-yl)ethylamino)-1,7-naphthyridine-3-carbonitrile, hydrochloride salt A microwave vial was charged with 4-(4-benzylphenylamino)-6-fluoro-1,7-naphthyridine-3-carbonitrile (0.100 g, 0.282 mmol), 1-N-BOC-4-(2-aminoethyl)piperazine and 2 mL THF, crimp-sealed, and heated in a microwave reactor at 180° C. for 35 minutes, until TLC analysis (5% MeOH in $CH_2Cl_2$) showed disappearance of the 6-fluoronaphthyridine. This process was repeated with 3 additional aliquots of the fluoronaphthyridine (0.120 g, 0.100 g, 0.100 g), and the contents of all 4 vials were then combined, partitioned between 50 mL each EtOAc and brine, and worked up as described above for the synthesis of WAY-191220. The crude product was purified by flash chromatography over silica gel (5% MeOH in $CH_2Cl_2$) and lyophilized to give pure 4-(4-benzylphenylamino)-6-(2-(1-N-BOC-piperazin-4-yl)ethylamino)-1,7-naphthyridine-3-carbonitrile (0.151 g, 23% yield): $^1H$ NMR (400 MHz, DMSO-$D_6$) δ 1.39 (s, 9 H) 2.34-2.44 (m, 4 H) 2.57 (t, J=6.6 Hz, 2 H) 3.21-3.42 (m, 6 H) 3.99 (s, 2 H) 6.59 (t, J=5.3 Hz, 1 H) 7.03 (s, 1 H) 7.14-7.34 (m, 9 H) 8.22 (s, 1 H) 8.81 (s, 1 H) 9.56 (s, 1 H).

A 50 mL round-bottomed flask containing the product of the previous step (0.151 g, 0.268 mmol) under an inert atmosphere was cooled to 0° C. in an ice bath, and 9 mL 4M HCl in dioxane was then added by syringe. The reaction mixture was stirred at 0° C. for 2 h, until TLC analysis (5% MeOH in $CH_2Cl_2$) showed complete disappearance of starting material. The solvent was then removed under reduced pressure, and the residue azeotroped with 9 mL dioxane and 27 mL toluene and dried in a vacuum oven overnight. The residue was then taken up in 50 mL MeOH and filtered to remove any insoluble impurities, evaporated, triturated with boiling MeCN/EtOH, and dried again in a vacuum oven for 3 days. This gave pure product as a bright yellow powder (39 mg, 29% yield): $^1H$ NMR (500 MHz, Pyridine-$D_5$) δ 2.62 (t, J=6.6 Hz, 2 H) 2.77-2.97 (m, 4 H) 3.19-3.49 (m, 6 H) 3.94 (s, 2 H) 7.23-7.36 (m, 8 H) 7.40 (d, J=8.2 Hz, 2 H) 8.64 (s, 1 H) 9.39 (s, 1 H); HRMS (ESI+) calcd for $C_{28}H_{30}N_7$ (MH+) 464.2557, found 464.2564.

Example 26

4-(3-cyanophenylamino)-6-(2-morpholinoethylamino)-1,7-naphthyridine-3-carbonitrile Following the procedure described above in Example 13, 4-chloro-6-fluoro-1,7-naphthyridine-3-carbonitrile (0.300 g, 1.45 mmol) was reacted with 3-aminobenzonitrile (0.188 g, 1.59 mmol). The crude product was purified by flash chromatography over silica gel (15-30% EtOAc in $CH_2Cl_2$) to give pure 4-(3-cyanophenylamino)-6-fluoro-1,7-naphthyridine-3-carbonitrile (0.122 g, 29% yield): $^1H$ NMR (400 MHz, DMSO-$D_6$) δ 7.57-7.80 (m, 3 H) 7.88 (s, 1 H) 8.16 (s, 1 H) 8.75 (s, 1 H) 9.11 (s, 1 H) 10.23 (s, 1 H).

The product of the first step (61.2 mg, 0.211 mmol) was reacted with 4-(2-aminoethyl)morpholine (0.550 g, 4.23 mmol) in 4.5 mL THF. After 1 hour, LC-MS analysis showed that some 6-fluoronaphthyridine remained, so additional amine (0.60 g, 4.61 mmol) was added, and the reaction heated for another hour. After work-up, the crude product was purified by recrystallization from EtOAc/EtOH to give tiny orange-yellow prisms (19.6 mg, 23% yield): $^1H$ NMR (400 MHz, DMSO-$D_6$) δ 2.43 (br s, 4 H) 2.55 (t, J=6.7 Hz, 2 H) 3.37 (q, J=6.2 Hz, 2 H) 3.50-3.62 (m, 4 H) 6.72 (t, J=5.3 Hz, 1 H) 6.97 (s, 1 H) 7.60 (d, J=4.6 Hz, 2 H) 7.66 (t, J=4.7 Hz, 1 H) 7.75 (s, 1 H) 8.35 (s, 1 H) 8.89 (s, 1 H) 9.75 (s, 1 H); HRMS (ESI+) calcd for $C_{22}H_{22}N_7O$ (MH+) 400.1881, found 400.1879.

Example 27

4-(4-benzoylphenylamino)-6-(2-morpholinoethylamino)-1,7-naphthyridine-3-carbonitrile Following the procedure described above in Example 1, 4-chloro-6-fluoro-1,7-naphthyridine-3-carbonitrile (0.150 g, 0.723 mmol) was reacted with 4-aminobenzophenone (0.157 g, 0.795 mmol) in 2 mL DME. Work-up gave 4-(4-benzoylphenylamino)-6-fluoro-1,7-naphthyridine-3-carbonitrile of sufficient purity to be used directly in the next step: $^1$H NMR (400 MHz, DMSO-D$_6$) δ 7.42-7.84 (m, 9 H) 8.17 (s, 1 H) 8.83 (s, 1 H) 9.15 (s, 1 H) 10.34 (s, 1 H).

The product from the previous step (0.206 g, 0.560 mmol) was reacted with 4-(2-aminoethyl)morpholine (1.47 mL, 1.46 g, 11.2 mmol). The crude product was purified twice by flash chromatography over silica gel (7-8% MeOH in CH$_2$Cl$_2$, then 5% MeOH in CH$_2$Cl$_2$), and lyophilized, to give a fluffy yellow solid (52 mg, 19% yield of 2 steps): $^1$H NMR (400 MHz, DMSO-D$_6$) δ 2.41 (br s, 4 H) 2.53 (t, J=5.8 Hz, 2 H) 3.37 (q, J=6.4 Hz, 2 H) 3.48-3.62 (m, 4 H) 6.79 (t, J=5.4 Hz, 1 H) 6.91 (s, 1 H) 7.31 (d, J=8.6 Hz, 2 H) 7.57 (t, J=7.5 Hz, 2 H) 7.65-7.70 (m, 1 H) 7.70-7.74 (m, 2 H) 7.77 (d, J=8.6 Hz, 2 H) 8.45 (s, 1 H) 8.93 (s, 1 H) 9.89 (s, 1 H); HRMS (ESI+) calcd for C$_{28}$H$_{27}$N$_6$O$_2$ (MH+) 479.2109, found 479.2202.

Example 28

6-(2-morpholinoethylamino)-4-(4-(phenylsulfonyl)phenylamino)-1,7-naphthyridine-3-carbonitrile Following the procedure described above in Example 1, 4-chloro-6-fluoro-1,7-naphthyridine-3-carbonitrile (0.150 g, 0.723 mmol) was reacted with 4-(phenylsulfonyl)aniline (0.185 g, 0.795 mmol) in 3 mL DME. Work-up gave 6-fluoro-4-(4-(phenylsulfonyl)phenylamino-1,7-naphthyridine-3-carbonitrile of sufficient purity to be used directly in the next step: $^1$H NMR (400 MHz, DMSO-D$_6$) δ 7.50-7.75 (m, 5 H) 7.90-8.01 (m, 4 H) 8.06 (s, 1 H) 8.86 (s, 1 H) 9.16 (s, 1 H) 10.30 (s, 1 H).

The product from the previous step (0.244 g, 0.603 mmol) was reacted with 4-(2-aminoethyl)morpholine (1.6 mL, 1.6 g, 12 mmol). The crude product was purified by flash chromatography over silica gel (5% MeOH in CH$_2$Cl$_2$), and lyophilized, to give a fluffy, bright yellow solid (44 mg, 14% yield of 2 steps): $^1$H NMR (400 MHz, DMSO-D$_6$) δ 2.38 (s, 4 H) 2.44-2.56 (m, 2 H) 3.28-3.37 (m, 2 H) 3.49-3.59 (m, 4 H) 6.77 (s, 1 H) 6.81 (t, J=5.3 Hz, 1 H) 7.27 (d, J=8.8 Hz, 2 H) 7.57-7.65 (m, 2 H) 7.65-7.72 (m, 1 H) 7.84-7.97 (m, 4 H) 8.48 (s, 1 H) 8.95 (s, 1 H) 9.88 (br s, 1 H).

Example 29

4-(3-methylphenylamino)-6-(pyridin-3-ylmethylamino)-1,7-naphthyridine-3-carbonitrile In a microwave vial, 4-chloro-6-fluoro-1,7-naphthyridine-3-carbonitrile (0.200 g, 0.963 mmol) and m-toluidine (0.11 mL, 0.11 g, 1.1 mmol) were taken up in 5 mL DME. The vial was crimp-sealed and heated in a microwave reactor at 140° C. for 10 minutes. 3-(aminomethyl)pyridine (2.0 mL, 2.1 g, 19 mmol) was then added, and the reaction was heated at 200° C. for 30 minutes. To work up the reaction, the vial contents were partitioned between EtOAc and brine. The aqueous layer was extracted with additional EtOAc, and the combined organic extracts washed with water and evaporated. The crude product was purified twice by preparative HPLC, and lyophilized to give a fluffy bright yellow solid (7.5 mg, 2.1% yield): $^1$H NMR (400 MHz, DMSO-D$_6$) δ 2.31 (s, 3 H) 4.55 (d, J=4.0 Hz, 2 H) 7.06 (s, 3 H) 7.16 (s, 1 H) 7.21-7.39 (m, 2 H) 7.44 (s, 1 H) 7.75 (d, J=7.6 Hz, 1 H) 8.22 (s, 1 H) 8.43 (s, 1 H) 8.59 (s, 1 H) 8.82 (s, 1 H) 9.61 (br s, 1 H).

Example 30

Methyl 4-(3-cyano-6-(pyridin-3-ylmethylamino)-1,7-naphthyridin-4-ylamino)benzoate Following the procedure described above in Example 29, 4-chloro-6-fluoro-1,7-naphthyridine-3-carbonitrile (0.200 g, 0.963 mmol) was reacted with methyl 4-aminobenzoate (0.16 g, 1.1 mmol), then with 3-(aminomethyl)pyridine. The crude product was purified by preparative HPLC and lyophilized to give a fluffy, bright yellow solid (9.7 mg, 2.5% yield): $^1$H NMR (400 MHz, DMSO-D$_6$) δ 3.86 (none, 1 H) 4.55 (d, J=6.1 Hz, 2 H) 7.03 (s, 1 H) 7.20 (d, J=8.1 Hz, 2 H) 7.31 (dd, J=7.6, 5.1 Hz, 1 H) 7.48-7.61 (m, 1 H) 7.71 (d, J=8.1 Hz, 1 H) 7.91 (d, J=8.3 Hz, 2 H) 8.35-8.46 (m, 2 H) 8.56 (s, 1 H) 8.89 (s, 1 H).

Example 31

4-(4-methoxyphenylamino)-6-(2-morpholinoethylamino)-1,7-naphthyridine-3-carbonitrile Following the procedure described above in Example 29, 4-chloro-6-fluoro-1,7-naphthyridine-3-carbonitrile (0.200 g, 0.963 mmol) was reacted with P-anisidine (0.13 g, 1.1 mmol), then with 3-(aminomethyl)pyridine. The crude product was purified by preparative HPLC and lyophilized to give a bright yellow solid (6.0 mg, 1.6% yield): $^1$H NMR (400 MHz, DMSO-D$_6$) δ 3.79 (s, 3 H) 4.56 (d, J=6.1 Hz, 2 H) 6.98 (d, J=8.6 Hz, 2 H) 7.19 (s, 1 H) 7.26 (d, J=8.8 Hz, 2 H) 7.34 (dd, J=7.6, 5.1 Hz, 1 H) 7.43 (t, J=6.6 Hz, 1 H) 7.77 (d, J=7.3 Hz, 1 H) 8.17 (s, 1 H) 8.44 (d, J=4.0 Hz, 1 H) 8.61 (s, 1 H) 8.81 (s, 1 H) 9.56 (s, 1 H).

Example 32

6-(pyridin-3-ylmethylamino)-4-(3-(trifluoromethoxy)phenylamino)-1,7-naphthyridine-3-carbonitrile Following the procedure described above in Example 29, 4-chloro-6-fluoro-1,7-naphthyridine-3-carbonitrile (0.200 g, 0.963 mmol) was reacted with 3-(trifluoromethoxy)aniline (0.14 mL, 0.19 g, 1.1 mmol), then with 3-(aminomethyl)pyridine. The crude product was purified by preparative HPLC and lyophilized to give a fluffy, bright yellow solid (1.5 mg, 0.36% yield): $^1$H NMR (400 MHz, DMSO-D$_6$) δ 4.56 (d, J=6.8 Hz, 2 H) 7.03-7.29 (m, 4 H) 7.33 (dd, J=8.0, 4.9 Hz, 1 H) 7.48 (br s, 2 H) 7.74 (d, J=7.3 Hz, 1 H) 8.31 (br s, 1 H) 8.43 (d, J=4.8 Hz, 1 H) 8.58 (s, 1 H) 8.87 (br s, 1 H) 9.73 (br s, 1 H).

Example 33

6-(pyridin-3-ylmethylamino)-4-(4-(trifluoromethoxy)phenylamino)-1,7-naphthyridine-3-carbonitrile Following the procedure described above in Example 29, 4-chloro-6-fluoro-1,7-naphthyridine-3-carbonitrile (0.200 g, 0.963 mmol) was reacted with 4-(trifluoromethoxy)aniline (0.14 mL, 0.19 g, 1.1 mmol), then with 3-(aminomethyl)pyridine. The crude product was purified twice by preparative HPLC, and lyophilized to give a fluffy, bright yellow solid (16 mg, 3.8% yield): $^1$H NMR (400 MHz, DMSO-D$_6$) δ 4.57 (d, J=6.6 Hz, 2 H) 7.12 (s, 1 H) 7.33 (dd, J=7.6, 4.8 Hz, 1 H) 7.38 (s, 4 H) 7.52 (t, J=6.1 Hz, 1 H) 7.75 (d, J=7.6 Hz, 1 H) 8.29 (s, 1 H) 8.43 (d, J=3.8 Hz, 1 H) 8.59 (s, 1 H) 8.86 (s, 1 H) 9.67 (s, 1 H).

Example 34

4-(3-Chloro-4-fluoro-phenylamino)-6-(2-morpholin-4-yl-ethylamino)-1,7-naphthyridine-3-carbonitrile A solution of 2-morpholin-4-yl-ethylamine (0.44 mL, 2.73 mmol) and 4-(3-Chloro-4-fluoro-phenylamino)-6-fluoro-[1,7]naphthyridine-3-carbonitrile (0.50 g, 1.58 mmol) in pyridine 5.3 mL was heated to 80° C. for 7 days. The solvent was evaporated and the crude product was purified by flash column chromatography (7% MeOH in $CHCl_3$) to give a yellow solid (0.18 g, 44%). 1H NMR (400 MHz, $CDCl_3$) δ 2.5 (m, 4 H) 2.6 (d, J=11.9 Hz, 2 H) 3.2 (m, 2 H) 3.7 (m, 4 H) 5.5 (t, J=5.1 Hz, 1 H) 6.2 (s, 1 H) 6.9 (s, 1 H) 7.1 (m, 1 H) 7.2 (t, J=8.6 Hz, 1 H) 7.3 (m, 1 H) 8.5 (s, 1 H) 9.1 (d, J=0.5 Hz, 1 H).

Example 35

6-amino-4-[(3-chloro-4-fluorophenyl)amino]-1,7-naphthyridine-3-carbonitrile

A solution of 4-[(3-chloro-4-fluorophenyl)amino]-6-[(4-methoxybenzyl)amino]-1,7-naphthyridine-3-carbonitrile (0.623 g, 1.45 mmol) and trifluoroacetic acid (14.5 mL) in methylene chloride 14.5 mL was stirred at room temperature overnight. The reaction was diluted with toluene and the solvents were evaporated. The crude product was purified by flash column chromatography (3% MeOH in $CHCl_3$) to give a yellow solid (0.287 g, 64%). 1H NMR (400 MHz, DMSO-D6) δ ppm 7.1 (s, 1 H) 7.3 (m, 1 H) 7.5 (t, J=9.0 Hz, 1 H) 7.6 (dd, J=6.2, 2.4 Hz, 1 H) 8.4 (s, 1 H) 8.8 (s, 1 H) 10.0 (s, 1 H)

Example 36

4-[(3-isopropylphenyl)amino]-6-(2-morpholin-4-ylethoxy)-1,7-naphthyridine-3-carbonitrile A solution of 4-chloro-6-fluoro-[1,7]naphthyridine-3-carbonitrile (0.75 g, 3.62 mmol) and 3-isopropylaniline (0.82 mL, 5.79 mmol) in ethanol (11 mL) was heated to 80° C. for 10 hours. The reaction was cooled to 0° C., water was added and the mixture was stirred for 15 minutes. The product was filtered, washed with water and dried in the vacuum oven to provide pure 6-fluoro-4-[(3-isopropylphenyl)amino]-1,7-naphthyridine-3-carbonitrile (0.88 g, 80%). 1H NMR (400 MHz, DMSO-D6) δ ppm 1.2 (d, J=7.1 Hz, 6 H) 2.9 (dq, J=6.9 Hz, 1 H) 7.2 (m, 3 H) 7.4 (t, J=7.8 Hz, 1 H) 8.2 (s, 1 H) 8.6 (s, 1 H) 9.1 (s, 1 H) 10.1 (s, 1 H).

To 6-fluoro-4-[(3-isopropylphenyl)amino]-1,7-naphthyridine-3-carbonitrile (0.050 g, 0.16 mmol) was added a 1 M solution of freshly prepared alkoxide of N-(2-hydroxyethyl)morpholine in THF (1.88 mL, 1.88 mmol). The reaction was heated to reflux for 2 hours. The solvent was evaporated and water was added. Diethyl ehter and methylene chloride was added and crystals formed. The product was collected by filtration to give a yellow solid (0.044 g, 66%). 1H NMR (400 MHz, DMSO-D6) δ ppm 1.2 (d, J=6.8 Hz, 6 H) 2.5 (m, 2 H) 2.7 (t, J=5.8 Hz, 2 H) 2.9 (m, 1 H) 3.3 (m, 2 H) 3.6 (m, 4 H) 4.5 (t, J=5.8 Hz, 2 H) 7.1 (m, 3 H) 7.3 (t, J=8.7 Hz, 1 H) 7.8 (s, 1 H) 8.4 (s, 1 H) 9.0 (s, 1 H) 9.9 (s, 1 H).

Example 37

4-[(3-isopropylphenyl)amino]-6-[(2-morpholin-4-ylethyl)amino]-1,7-naphthyridine-3-carbonitrile Following the procedure described above in Example 34, 6-fluoro-4-[(3-isopropylphenyl)amino]-1,7-naphthyridine-3-carbonitrile was reacted with 2-morpholin-4-yl-ethylamine in pyridine. The crude product was purified by flash column chromatography (1% methanol in methylene chloride) to give a yellow solid (0.15 g, 54%). 1H NMR (400 MHz, DMSO-D6) δ ppm 1.2 (d, J=7.1 Hz, 6 H) 2.4 (m, 4 H) 2.6 (m, 2 H) 2.9 (dq, J=6.9 Hz, 1 H) 3.4 (m, 2 H) 3.6 (m, 4 H) 6.6 (t, J=5.4 Hz, 1 H) 7.1 (m, 4 H) 7.3 (t, J=8.0 Hz, 1 H) 8.2 (s, 1 H) 8.8 (s, 1 H) 9.6 (s, 1 H)

Example 38

4-[(3-isopropylphenyl)amino]-6-[(4-methoxybenzyl)amino]-1,7-naphthyridine-3-carbonitrile Following the procedure described above in Example 34, 6-fluoro-4-[(3-isopropylphenyl)amino]-1,7-naphthyridine-3-carbonitrile was reacted with (4-methoxyphenyl)methanamine. The crude product was purified by flash column chromatography (1% methanol in methylene chloride) to give a yellow solid (0.209 g, 25%). 1H NMR (400 MHz, DMSO-D6) δ ppm 1.2 (d, J=6.8 Hz, 6 H) 2.8 (none, 1 H) 2.9 (dq, J=6.9 Hz, 1 H) 3.7 (s, 3 H) 4.4 (d, J=6.3 Hz, 2 H) 6.9 (m, 2 H) 7.1 (m, 2 H) 7.1 (dd, J=4.3, 2.5 Hz, 2 H) 7.3 (m, 4 H) 8.2 (s, 1 H) 8.8 (s, 1 H) 9.6 (s, 1 H)

Example 39

4-[(3-chloro-4-fluorophenyl)amino]-6-(2-morpholin-4-ylethoxy)-1,7-naphthyridine-3-carbonitrile Following the procedure described above in Example 36, 4-(3-Chloro-4-fluoro-phenylamino)-6-fluoro-[1,7]naphthyridine-3-carbonitrile was reacted with a 1 M solution of freshly prepared alkoxide of N-(2-hydroxyethyl)morpholine in THF. The product was collected by filtration to give a yellow solid (0.015 g, 8%). 1H NMR (400 MHz, DMSO-D6) δ ppm 2.5 (m, 2 H) 2.7 (t, J=5.7 Hz, 2 H) 3.6 (m, 6 H) 4.3 (t, J=5.8 Hz, 2 H) 6.7 (ddd, J=8.7, 4.4, 2.5 Hz, 1 H) 6.8 (dd, J=6.8, 2.5 Hz, 1 H) 7.1 (dd, J=9.5, 8.7 Hz, 1 H) 7.4 (d, J=0.8 Hz, 1 H) 7.7 (s, 1 H) 8.4 (d, J=0.8 Hz, 1 H).

Example 40

4-[(3-chloro-4-fluorobenzyl)amino]-6-[(2-morpholin-4-ylethyl)amino]-1,7-naphthyridine-3-carbonitrile 4-[(3-chloro-4-fluorobenzyl)amino]-6-fluoro-1,7-naphthyridine-3-carbonitrile was prepared according to the procedure for 6-fluoro-4-[(3-isopropylphenyl)amino]-1,7-naphthyridine-3-carbonitrile in Example 36. The product was filtered, washed with cold ethanol and dried in the vacuum oven to provide pure product (0.356 g, 45%). 1H NMR (400 MHz, DMSO-D6) δ ppm 5.0 (d, J=6.3 Hz, 2 H) 7.4 (m, 2 H) 7.6 (dd, J=6.8, 1.8 Hz, 1 H) 8.2 (s, 1 H) 8.6 (s, 1 H) 8.9 (t, J=6.4 Hz, 1 H) 9.0 (s, 1 H).

Following the procedure described above in Example 34, 4-[(3-chloro-4-fluorobenzyl)amino]-6-fluoro-1,7-naphthyridine-3-carbonitrile was reacted with 2-morpholin-4-ylethylamine. The crude product was purified by flash column chromatography (1% methanol in methylene chloride) to give a yellow solid (0.14 g, 48%). 1H NMR (400 MHz, DMSO-D6) δ ppm 2.4 (m, 4 H) 2.6 (m, 2 H) 3.4 (m, 2 H) 3.6 (m, 4 H) 5.0 (d, J=7.1 Hz, 2 H) 6.5 (m, 1 H) 7.0 (s, 1 H) 7.3 (m, 1 H) 7.4 (m, 1 H) 7.5 (dd, J=6.9, 1.9 Hz, 1 H) 8.1 (s, 1 H) 8.5 (m, 1 H) 8.8 (s, 1 H).

Example 41

6-[(2-morpholin-4-ylethyl)amino]-4-[(4-phenoxyphenyl)amino]-1,7-naphthyridine-3-carbonitrile 6-Fluoro-4-(4-phenoxy-phenylamino)-[1,7]naphthyridine-3-carbonitrile was prepared according to the procedure for 6-fluoro-4-[(3-isopropylphenyl)amino]-1,7-naphthyridine-3-carbonitrile in Example 36. The product was filtered, washed with cold ethanol and dried in the vacuum oven to provide pure product (0.324 g, 94%). 1H NMR (400 MHz, DMSO-D6) δ ppm 7.1 (m, 2 H) 7.1 (m, 3 H) 7.4 (m, 4 H) 8.2 (s, 1H) 8.6 (s, 1 H) 9.1 (s, 1 H) 10.1 (m, 1 H).

Following the procedure described above in Example 34, 6-Fluoro-4-(4-phenoxy-phenylamino)-[1,7]naphthyridine-3-carbonitrile was reacted with 2-morpholin-4-yl-ethylamine. The crude product was purified by flash column chromatography (2% methanol in methylene chloride) to give a yellow solid (0.12 g, 44%). 1H NMR (400 MHz, DMSO-D6) δ ppm 2.5 (m, 4 H) 2.6 (t, J=6.8 Hz, 2 H) 3.4 (m, 2 H) 3.6 (m, 4 H) 6.6 (t, J=5.6 Hz, 1 H) 7.0 (m, 2 H) 7.1 (m, 4 H) 7.4 (m, 3 H) 8.2 (s, 1 H) 8.3 (s, 1 H) 8.8 (s, 1 H) 9.6 (s, 1 H).

Example 42

6-[(2-morpholin-4-ylethyl)amino]-4-{[4-(trifluoromethyl)phenyl]amino}-1,7-naphthyridine-3-carbonitrile 6-fluoro-4-{[4-(trifluoromethyl)phenyl]amino}-1,7-naphthyridine-3-carbonitrile was prepared according to the procedure for 6-fluoro-4-[(3-isopropylphenyl)amino]-1,7-naphthyridine-3-carbonitrile in Example 36. The product was filtered, washed with cold ethanol and dried in the vacuum oven to provide pure product (0.2136 g, 66%). 1H NMR (400 MHz, DMSO-D6) δ ppm 7.5 (m, 2 H) 7.8 (d, J=9.1 Hz, 2 H) 8.2 (s, 1 H) 8.8 (s, 1 H) 9.1 (s, 1 H) 10.3 (m, 1 H).

Following the procedure described above in Example 34, 6-fluoro-4-{[4-(trifluoromethyl)phenyl]amino}-1,7-naphthyridine-3-carbonitrile was reacted with 2-morpholin-4-yl-ethylamine. The crude product was purified by flash column chromatography (2% methanol in methylene chloride) to give a yellow solid (0.14 g, 55%). 1H NMR (400 MHz, DMSO-D6) δ ppm 2.4 (m, 4 H) 3.4 (m, 2 H) 3.4 (m, 2 H) 3.6 (m, 4 H) 6.8 (m, 1 H) 6.9 (s, 1 H) 7.4 (d, J=8.3 Hz, 2 H) 7.7 (d, J=8.6 Hz, 2 H) 8.4 (s, 1 H) 8.9 (s, 1 H) 9.8 (s, 1 H).

Example 43

4-[(4-isopropylphenyl)amino]-6-[(2-morpholin-4-ylethyl)amino]-1,7-naphthyridine-3-carbonitrile 6-fluoro-4-[(4-isopropylphenyl)amino]-1,7-naphthyridine-3-carbonitrile was prepared according to the procedure for 6-fluoro-4-[(3-isopropylphenyl)amino]-1,7-naphthyridine-3-carbonitrile in Exam[;e 36. The product was filtered, washed with cold ethanol and dried in the vacuum oven to provide pure product (0.159 g, 63%). 1H NMR (400 MHz, DMSO-D6) δ ppm 1.2 (d, J=6.8 Hz, 6 H) 3.0 (m, 1 H) 7.3 (m, 4 H) 8.2 (s, 1 H) 8.6 (s, 1 H) 9.0 (s, 1 H) 10.0 (m, J=2.1, 2.1 Hz, 1 H).

Following the procedure described above in Example 34, 6-fluoro-4-[(4-isopropylphenyl)amino]-1,7-naphthyridine-3-carbonitrile was reacted with 2-morpholin-4-yl-ethylamine. The crude product was purified by flash column chromatography (2% methanol in methylene chloride) to give a yellow solid (0.11 g, 55%). 1H NMR (400 MHz, DMSO-D6) δ ppm 1.2 (d, J=6.8 Hz, 6 H) 2.4 (m, 4 H) 2.6 (m, 2 H) 2.9 (qt, 1 H) 3.3 (m, 1 H) 3.4 (m, 1 H) 3.6 (m, 4 H) 6.6 (m, 1 H) 7.0 (s, 1 H) 7.2 (d, J=8.6 Hz, 2 H) 7.3 (m, 2 H) 8.2 (s, 1 H) 8.8 (s, 1 H) 9.5 (s, 1 H).

Example 44

4-(1H-indol-5-ylamino)-6-[(2-morpholin-4-ylethyl)amino]-1,7-naphthyridine-3-carbonitrile 6-fluoro-4-(1H-indol-5-ylamino)-1,7-naphthyridine-3-carbonitrile was prepared according to the procedure for 6-fluoro-4-[(3-isopropylphenyl)amino]-1,7-naphthyridine-3-carbonitrile in Example 36. The product was filtered, washed with cold ethanol and dried in the vacuum oven to provide pure product (0.229 g, 78%). 1H NMR (400 MHz, DMSO-D6) δ ppm 6.5 (m, 1 H) 7.1 (dd, J=8.5, 1.9 Hz, 1 H) 7.4 (t, 1 H) 7.5 (d, J=8.3 Hz, 1 H) 7.6 (d, J=1.5 Hz, 1 H) 8.3 (s, 1 H) 8.5 (s, 1 H) 9.0 (s, 1 H) 10.1 (s, 1 H) 11.3 (s, 1 H).

Following the procedure described above in Example 34, 6-fluoro-4-(1H-indol-5-ylamino)-1,7-naphthyridine-3-carbonitrile was reacted with 2-morpholin-4-yl-ethylamine. The crude product was purified by flash column chromatography (2 to 10% methanol in methylene chloride) to give a yellow solid (0.103 g, 55%). 1H NMR (400 MHz, DMSO-D6) δ ppm 2.4 (m, 4 H) 2.6 (t, J=6.8 Hz, 2 H) 3.4 (m, 2 H) 3.6 (m, 4 H) 6.5 (m, 2 H) 7.1 (dd, J=8.5, 1.9 Hz, 1 H) 7.2 (s, 1 H) 7.4 (m, 1 H) 7.4 (d, J=8.6 Hz, 1 H) 7.5 (d, J=1.8 Hz, 1 H) 8.1 (s, 1 H) 8.8 (s, 1 H) 9.7 (s, 1 H) 11.2 (s, 1 H).

Example 45

4-[(3-chloro-4-fluorophenyl)amino]-6-{[3-(4-methylpiperazin-1-yl)propyl]amino}-1,7-naphthyridine-3-carbonitrile Following the procedure described above in Example 34, 4-(3-Chloro-4-fluoro-phenylamino)-6-fluoro-[1,7]naphthyridine-3-carbonitrile was reacted with 3-(4-methylpiperazin-1-yl)propan-1-amine. The crude product was purified by flash column chromatography (10% methanol in methylene chloride) to give a yellow solid (0.102 g, 71%). 1H NMR (400 MHz, DMSO-D6) δ ppm 1.8 (m, 2 H) 2.2 (s, 3 H) 2.4 (m, 8 H) 3.3 (m, 4 H) 6.9 (m, 2 H) 7.4 (s, 1 H) 7.5 (t, J=9.0 Hz, 1 H) 7.6 (d, J=7.1 Hz, 1 H) 8.3 (s, 1 H) 8.8 (s, 1 H) 9.7 (s, 1 H).

Example 47

6-(benzylamino)-4-[(3-chloro-4-fluorophenyl)amino]-1,7-naphthyridine-3-carbonitrile Following the procedure described above in Example 34, 4-(3-Chloro-4-fluoro-phenylamino)-6-fluoro-[1,7]naphthyridine-3-carbonitrile was reacted with benzylamine. The crude product was purified by flash column chromatography (1% methanol in methylene chloride) to give a yellow solid (0.051 g, 54%). 1H NMR (400 MHz, DMSO-D6) δ ppm 4.5 (d, J=6.3 Hz, 2 H) 7.0 (s, 1 H) 7.2 (t, J=7.2 Hz, 1 H) 7.3 (m, 5 H) 7.5 (m, 2 H) 7.6 (dd, J=6.6, 2.5 Hz, 1 H) 8.3 (s, 1 H) 8.9 (s, 1 H) 9.6 (s, 1 H).

Example 48

4-[(3-chloro-4-fluorophenyl)amino]-6-{[3-(dimethylamino)propyl]amino}-1,7-naphthyridine-3-carbonitrile Following the procedure described above in Example 34, 4-(3-Chloro-4-fluoro-phenylamino)-6-fluoro-[1,7]naphthyridine-3-carbonitrile was reacted with $N^1,N^1$-dimethylpropane-1,3-diamine. The crude product was purified by flash column chromatography (15% methanol in methylene chloride) to give a yellow solid (0.040 g, 44%). 1H NMR (400 MHz, chloroform-D) δ ppm 1.8 (m, 2 H) 2.3 (s, 6 H) 2.4 (t, J=6.4 Hz, 2 H) 3.2 (t, J=6.6 Hz, 2 H) 3.5 (s, 1 H) 6.3 (s, 1 H) 7.1 (m, 2 H) 7.2 (t, J=8.6 Hz, 1 H) 7.3 (dd, J=6.3, 2.8 Hz, 1 H) 8.4 (s, 1 H) 9.0 (s, 1 H).

Example 49

4-[(3-chloro-4-fluorophenyl)amino]-6-[(3-morpholin-4-ylpropyl)amino]-1,7-naphthyridine-3-carbonitrile Following the procedure described above in Example 34, 4-(3-Chloro-4-fluoro-phenylamino)-6-fluoro-[1,7]naphthyridine-3-carbonitrile was reacted with 3-morpholinopropan-1-amine. The crude product was purified by flash column chromatography (5% methanol in methylene chloride) to give a yellow solid (0.065 g, 65%). 1H NMR (400 MHz, DMSO-D6) δ ppm 1.8 (m, 2 H) 2.4 (d, J=13.1 Hz, 6 H) 3.3 (dd, J=12.9, 6.8 Hz, 2 H) 3.6 (m, 4 H) 6.9 (m, 2 H) 7.3 (m, 1 H) 7.5 (t, J=9.0 Hz, 1 H) 7.6 (dd, J=6.8, 2.5 Hz, 1 H) 8.3 (s, 1 H) 8.8 (s, 1 H) 9.7 (s, 1 H).

Example 50

4-[(3-chloro-4-fluorophenyl)amino]-6-[(3-hydroxypropyl)amino]-1,7-naphthyridine-3-carbonitrile Following the procedure described above in Example 34, 4-(3-Chloro-4-fluoro-phenylamino)-6-fluoro-[1,7]naphthyridine-3-carbonitrile was reacted with 3-aminopropan-1-ol. The crude product was purified by flash column chromatography (1% methanol in methylene chloride) to give a yellow solid (0.048 g, 55%). 1H NMR (400 MHz, DMSO-D6) δ ppm 1.8 (m, 2 H) 3.3 (d, J=6.3 Hz, 4 H) 3.5 (m, 2 H) 6.9 (m, 1 H) 7.0 (s, 1 H) 7.4 (m, 1 H) 7.5 (t, J=9.2 Hz, 1 H) 7.6 (m, 1 H) 8.3 (s, 1 H) 8.8 (s, 1 H).

Example 51

4-[(3-chloro-4-fluorophenyl)amino]-6-{[(1R)-1-phenylpropyl]amino}-1,7-naphthyridine-3-carbonitrile In a microwave vial, 4-chloro-6-fluoro-1,7-naphthyridine-3-carbonitrile (1.3 g, 6 mmol) and 3-chloro-4-fluoroaniline (1.0 g, 6.9 mmol) were taken up in DME. The vial was crimp-sealed and heated in a microwave reactor at 140° C. for 15 minutes. This was repeated with another two batches of reagents. The contents of the three vials were transferred together to a separatory funnel and partitioned between EtOAc and 10% Na$_2$CO$_3$, and the aqueous layer extracted two additional times with EtOAc. The combined organic extracts were washed with brine, dried over anhydrous Na$_2$SO$_4$, filtered and evaporated to give 4-(3-chloro-4-fluorophenylamino)-6-fluoro-1,7-naphthyridine-3-carbonitrile of sufficient purity to be used directly in the next step (4.6 g, 75.3% yield): 1H NMR (400 MHz, DMSO-D$_6$) δ 7.32-7.49 (m, 1 H) 7.53 (t, J=9.0 Hz, 1 H) 7.72 (dd, J=6.3, 2.3 Hz, 1 H) 8.16 (s, 1 H) 8.69 (s, 1 H) 9.08 (s, 1 H) 10.14 (s, 1 H).

The product of the first step (0.15 g, 0.47 mmol) was taken up in (R)-(+)-1-phenylpropylamine (2.0 mL, 1.86 g, 13.8 mmol) in a microwave vial. The sealed vial was heated in a microwave reactor at 180° C. for 95 min, reaction was monitored by LC/MS. The reaction was stopped and toluene was added to chase off excess starting material amine. The crude product was purified by preparative HPLC, and lyophilized to give a fluffy, yellow solid (94 mg, 46.3% yield): 1H NMR (400 MHz, MeOD) δ ppm 0.99 (t, J=7.33 Hz, 3 H) 1.81-1.98 (m, 2 H) 4.59 (t, J=7.07 Hz, 1 H) 6.72 (s, 1 H) 7.15-7.37 (m, 7 H) 7.40 (dd, J=2.40 Hz, 1 H) 8.22 (s, 1 H) 8.81 (d, J=0.76 Hz, 1 H); HRMS (ESI+) calcd for C$_{24}$H$_{19}$ClFN$_5$ 432.13858, found (MH+) 432.1389.

Example 52

4-[(3-chloro-4-fluorophenyl)amino]-6-{[(1S)-1-phenylpropyl]amino}-1,7-naphthyridine-3-carbonitrile Following the procedure described above in Example 51, 4-(3-Chloro-4-fluoro-phenylamino)-6-fluoro-[1,7]naphthyridine-3-carbonitrile (0.15 g, 0.47 mmol) was reacted with (s)-(−)-1-phenylpropylamine (2.0 mL, 1.86 g, 13.8 mmol) in a sealed vial heated in a microwave reactor at 185° C. for 90 min. The crude product was purified by preparative HPLC and lyophilized to give a fluffy, yellow solid (82 mg, 40.4% yield): 1H NMR (400 MHz, MeOD) δ ppm 0.99 (t, J=7.45 Hz, 3 H) 1.78-2.01 (m, 2 H) 4.58 (t, J=7.20 Hz, 1 H) 6.72 (s, 1 H) 7.14-7.37 (m, 7 H) 7.40 (dd, J=2.53 Hz, 1 H) 8.22 (s, 1 H) 8.81 (s, 1 H); HRMS (ESI+) calcd for C$_{24}$H$_{19}$ClFN$_5$ 432.13858; found (MH+) 432.1391.

Example 53

4-[(3-chloro-4-fluorophenyl)amino]-6-{[(1R, 2S)-2-hydroxy-1-methyl-2-phenylethyl]amino}-1,7-naphthyridine-3-carbonitrile Following the procedure described above in Example 51, 4-(3-Chloro-4-fluoro-phenylamino)-6-fluoro-[1,7]naphthyridine-3-carbonitrile (0.10 g, 0.32 mmol) was reacted with (1S, 2R)-(+) norephdrine (0.96 g, 6.32 mmol) in 2 mL of THF. The reaction mixture was heated in a sealed vial in a microwave reactor at 140° C. for 50 min, then heated to 160° C. for 30 min. The crude product was purified by preparative HPLC and lyophilized to give a fluffy, yellow solid (26.4 mg, 18.7% yield): 1H NMR (400 MHz, DMSO-D6) δ ppm 1.03 (d, J=6.32 Hz, 3 H) 3.87-4.02 (m, 1 H) 4.67 (t, J=4.67 Hz, 1 H) 5.46 (d, J=4.29 Hz, 1 H) 6.43 (d, J=9.35 Hz, 1 H) 6.93 (s, 1 H) 7.12 (t, J=7.33 Hz, 1 H) 7.18-7.46 (m, 6 H) 7.48-7.55 (m, 1 H) 8.19 (s, 1 H) 8.75 (s, 1 H) 9.54 (s, 1 H); HRMS (ESI+) calcd for C$_{24}$H$_{19}$ClFN$_5$O 448.13349, found (MH+), 448.1334.

Example 54

4-[(3-chloro-4-fluorophenyl)amino]-6-{[(1S, 2R)-2-hydroxy-1-methyl-2-phenylethyl]amino}-1,7-naphthyridine-3-carbonitrile Following the procedure described above in Example 51, 4-(3-Chloro-4-fluoro-phenylamino)-6-fluoro-[1,7]naphthyridine-3-carbonitrile (0.10 g, 0.32 mmol) was reacted with (1R, 2S)-(−) norephdrine (0.96 g, 6.32 mmol) in 2 mL of THF. The reaction mixture was heated up in a sealed vial in a microwave reactor at 140° C. for 105 min. The crude product was purified by preparative HPLC and lyophilized to give a fluffy, yellow solid (26.7 mg, 18.9% yield): 1H NMR (400 MHz, DMSO-D6) δ ppm 1.09 (d, J=6.32 Hz, 3 H) 3.94-4.06 (m, 1 H) 4.73 (t, J=4.80 Hz, 1 H) 5.52 (d, J=4.29 Hz, 1 H) 6.49 (d, J=9.35 Hz, 1 H) 6.98 (s, 1 H) 7.18 (t, J=7.20 Hz, 1 H) 7.22-7.51 (m, 6 H) 7.58 (d, J=4.29 Hz, 1 H) 8.25 (s, 1 H) 8.81 (s, 1 H) 9.60 (s, 1 H); HRMS (ESI+) calcd for C$_{24}$H$_{19}$ClFN$_5$O 448.13349, found (MH+) 448.1334.

Example 55

4-[(3-chloro-4-fluorophenyl)amino]-6-{[(2R)-2-hydroxypropyl]amino}-1,7-naphthyridine-3-carbonitrile Following the procedure described above in Example 51, 4-(3-Chloro-4-fluoro-phenylamino)-6-fluoro-[1,7]naphthyridine-3-carbonitrile (0.10 g, 0.32 mmol) was reacted with (R)-1-amino-2-propanol (0.47 g, 6.32 mmol) in 2 mL of THF. The reaction mixture was heated up in a sealed vial in a microwave reactor at 140° C. for 40 min. The crude product was purified by preparative HPLC and lyophilized to give a yellow solid (20.7 mg, 17.6% yield): 1H NMR (400 MHz, DMSO-D6) δ ppm 1.08 (d, J=6.32 Hz, 3 H) 3.08-3.20 (m, 2 H) 3.76-3.90 (m, 1 H) 4.73 (d, J=4.55 Hz, 1 H) 6.55-6.68 (m, 1 H) 6.95 (s, 1 H) 7.25-7.34 (m, 1 H) 7.36-7.47 (m, 1 H) 7.50-7.60 (m, 1 H) 8.21 (s, 1 H) 8.78 (s, 1 H) 9.60 (s, 1 H); HRMS (ESI+) calcd for $C_{18}H_{15}ClFN_5O$ 372.10219, found (MH+) 372.1019.

Example 56

4-[(3-chloro-4-fluorophenyl)amino]-6-{[(2S)-2-hydroxypropyl]amino}-1,7-naphthyridine-3-carbonitrile Following the procedure described above in Example 51, 4-(3-Chloro-4-fluoro-phenylamino)-6-fluoro-[1,7]naphthyridine-3-carbonitrile (0.10 g, 0.32 mmol) was reacted with (S)-1-amino-2-propanol (0.47 g, 6.32 mmol) in 2 mL of THF. The reaction mixture was heated up in a sealed vial in a microwave reactor at 140° C. for 40 min. The crude product was purified by preparative HPLC and lyophilized to give a yellow solid (20.8 mg, 17.7% yield): 1H NMR (400 MHz, DMSO-D6) δ ppm 0.93 (d, J=6.32 Hz, 3 H) 2.96-3.03 (m, 2 H) 3.68 (s, 1 H) 4.58 (s, 1 H) 6.46 (m, 1 H) 6.80 (s, 1 H) 7.06-7.17 (m, 1 H) 7.21-7.33 (m, 1 H) 7.33-7.47 (m, 1 H) 8.05 (s, 1 H) 8.62 (s, 1 H) 9.44 (s, 1 H); HRMS (ESI+) calcd for $C_{18}H_{15}ClFN_5O$ 372.10219, found (MH+) 372.1019.

Example 57

4-[(3-chloro-4-fluorophenyl)amino]-6-{[(1S)-1-phenylethyl]amino}-1,7-naphthyridine-3-carbonitrile Following the procedure described above in Example 1, 4-(4-Chloro-3-fluoro-phenylamino)-6-fluoro-[1,7]naphthyridine-3-carbonitrile (168 mg, 0.5 mmol, 1 eq) was reacted with (1S)-1-phenylethylamine (1.3 mL, 10 mmol, 20 eq). The crude product was purified via preparative HPLC to obtain 48 mg product (23% yield).

Example 58

4-[(3-chloro-4-fluorophenyl)amino]-6-{[(1S)-2-morpholin-4-yl-1-phenylethyl]amino}-1,7-naphthyridine-3-carbonitrile Following the procedure described above in Example 1, 4-(4-Chloro-3-fluoro-phenylamino)-6-fluoro-[1,7]naphthyridine-3-carbonitrile (80 mg, 0.25 mmol, 1 eq) was reacted with (1S)-2-morpholin-4-yl-1-phenylethylamine (400 mg, 2 mmol, 8 eq). The crude product was purified via preparative HPLC to obtain 7 mg product (6% yield):
HRMS (ESI+) calcd for $C_{27}H_{24}ClFN_6O$ 503.1757 (M+H). found 503.1755 (M+H).

Example 59

4-[(3-chloro-4-fluorophenyl)amino]-6-{[(1R)-1-phenylethyl]amino}-1,7-naphthyridine-3-carbonitrile Following the procedure described above in Example 1, 4-(4-Chloro-3-fluoro-phenylamino)-6-fluoro-[1,7]naphthyridine-3-carbonitrile (73 mg, 0.23 mmol, 1 eq) was reacted with (1R)-1-phenylethylamine (993 mg, 4.6 mmol, 20 eq). The crude product was purified via preparative HPLC to obtain 25 mg product (35% yield): HRMS (ESI+) calcd for $C_{23}H_{17}ClFN_5$ 418.1230 (M+H), found (M+H) 418.1231.

Example 60

4-[(3-chloro-4-fluorophenyl)amino]-6-[(2-morpholin-4-yl-1-phenylethyl)amino]-1,7-naphthyridine-3-carbonitrile Following the procedure described above in Example 1, 4-(4-Chloro-3-fluoro-phenylamino)-6-fluoro-[1,7]naphthyridine-3-carbonitrile (53 mg, 0.17 mmol, 1 eq) was reacted with 2-morpholin-4-yl-1-phenylethylamine (700 mg, 3.4 mmol, 20 eq). The crude product was purified via preparative HPLC to obtain 60 mg product (54% yield):
HRMS (ESI+) calcd for $C_{27}H_{24}ClFN_6O$ 503.1757 (M+H). found (M+H) 503.1743.

Example 61

6-[(2-amino-6-fluorobenzyl)amino]-4-[(3-chloro-4-fluorophenyl)amino]-1,7-naphthyridine-3-carbonitrile Following the procedure described above in Example 1, 4-(4-Chloro-3-fluoro-phenylamino)-6-fluoro-[1,7]naphthyridine-3-carbonitrile (316 mg, 1 mmol, 1 eq) was reacted with 2-amino-6-fluorobenzylamine (2.5 g, 18 mmol, 18 eq) in THF (2 mL). The reaction mixture was diluted with a 1:1 mixture of acetonitrile and water and the yellow precipitate was collected by filtration. The solid was triturated with hexanes/ether to give 86 mg product as a light yellow solid (20% yield): HRMS (ESI+) calcd for $C_{22}H_{15}ClF_2N_6$ 437.1088 (M+H), found (M+H) 437.1078.

Example 62

4-[(3,4-dichlorophenyl)amino]-6-[(2-morpholin-4-ylethyl)amino]-1,7-naphthyridine-3-carbonitrile Following the procedure described above in Example 1, 4-Chloro-6-fluoro-[1,7]naphthyridine-3-carbonitrile (1.25 g, 6 mmol, 1 eq) was reacted with 3,4-dichloroaniline (1.06 g, 6.6 mmol, 1.1 eq) in DME (5 mL). The crude product was recrystallized from ether/ethyl acetate to obtain 1.26 g 4-(3,4-dichlorophenylamino)-6-fluoro-1,7-naphthyridine-3-carbonitrile (63% yield): HRMS (ESI+) calcd for $C_{15}H_7ClFN_4$ 333.0105 (M+H), found (M+H) 333.0104.

Following the procedure described above in Example 1, 4-(3,4-dichlorophenylamino)-6-fluoro-1,7-naphthyridine-3-carbonitrile (300 mg, 1.1 mmol, 1 eq) was reacted with 2-morpholin-4-yl-1-ethylamine (3 mL, 20 eq). The crude product was purified via preparative HPLC to obtain 60 mg product (13% yield):
HRMS (ESI+) calcd for $C_{21}H_{14}Cl_2FN_6O$ 443.1149 (M+H). found (M+H) 443.1141.

Example 63

4-[(3,4-dichlorophenyl)amino]-6-[(pyridin-3-ylmethyl)amino]-1,7-naphthyridine-3-carbonitrile Following the procedure described above in Example 1, 4-(3,4-dichlorophenylamino)-6-fluoro-[1,7]naphthyridine-3-carbonitrile (300 mg, 1.1 mmol, 1 eq) was reacted with pyridine-3-ylmethylamine (2.8 mL, 20 eq). The crude product was purified via preparative HPLC to obtain 41 mg product (11% yield): HRMS (ESI+) calcd for $C_{21}H_{14}Cl_2N_6$ 421.0730 (M+H), found (M+H) 421.0723.

Example 64

4-[(3-bromo-4-methylphenyl)amino]-6-[(2-morpholin-4-ylethyl)amino]-1,7-naphthyridine-3-carbonitrile Following the procedure described above in Example 1, 4-Chloro-3,6-difluoro-[1,7]naphthyridine-3-carbonitrile (1.25 g, 6 mmol, 1 eq) was reacted with 3-bromo-4-methylaniline (0.9 g, 6.6 mmol, 1.1 eq) in DME (5 mL). The crude product was recrystallized from ethyl acetate to obtain 1.3 g 4-[(3-bromo-4-methylphenyl)amino]-6-fluoro-1,7-naphthyridine-3-carbonitrile (61% yield): HRMS (ESI+) calcd for $C_{16}H_{10}BrFN_4$ 357.0145 (M+H), found (M+H) 357.0146

Following the procedure described above in Example 1, 4-[(3-bromo-4-methylphenyl)amino]-6-fluoro-[1,7]naphthyridine-3-carbonitrile (300 mg, 1.1 mmol, 1 eq) was reacted with 2-morpholin-4-yl-1-ethylamine (3 mL, 20 eq). The crude product was purified via preparative HPLC to obtain 67 mg product (18% yield):

HRMS (ESI+) calcd for $C_{22}H_{23}BrN_6O$ 467.1190 (M+H). found (M+H) 467.1186.

Example 65

4-[(3-bromo-4-methylphenyl)amino]-6-{[(1R)-1-phenylethyl)amino])}-1,7-naphthyridine-3-carbonitrile Following the procedure described above in Example 1, 4-[(3-bromo-4-methylphenyl)amino]-6-fluoro-[1,7]naphthyridine-3-carbonitrile (300 mg, 1.1 mmol, 1 eq) was reacted with (1R)-1-phenylethyl)amine (3 mL, 20 eq). The crude producrt was purified via preparative HPLC to obtain 77 mg product (20% yield): HRMS (ESI+) calcd for $C_{24}H_{20}BrN_5$ 458.0970 (M+H), found (M+H) 458.0975.

Example 66

4-[(3-bromo-4-methylphenyl)amino]-6-[(pyridine-3-ylmethyl)amino]-1,7-naphthyridine-3-carbonitrile Following the procedure described above in Example 1, 4-[(3-bromo-4-methylphenyl)amino]-6-fluoro-[1,7]naphthyridine-3-carbonitrile (300 mg, 1.1 mmol, 1 eq) was reacted with pyridine-3-ylmethylamine (2.8 mL, 20 eq). The crude product was purified via preparative HPLC to obtain 55 mg product (14% yield): HRMS (ESI+) calcd for $C_{22}H_{17}BrN_6$ 445.0771 (M+H), found (M+H) 445.0761.

Example 67

4-[(3,5-dichlorophenyl)amino]-6-[(2-morpholin-4-ylethyl)amino]-1,7-naphthyridine-3-carbonitrile Following the procedure described above in Example 1, 4-Chloro-3,6-difluoro-[1,7]naphthyridine-3-carbonitrile (1.25 g, 6 mmol, 1 eq) was reacted with 3,5-dichloroaniline (1.06 g, 6.6 mmol, 1.1 eq) in DME (5 mL). The crude product was recrystallized from methanol/ethyl acetate to obtain 1.4 g 4-[(3,5-dichlorophenyl)amino]-6-fluoro-1,7-naphthyridine-3-carbonitrile (70% yield): HRMS (ESI+) calcd for $C_{15}H_7ClFN_4$ 333.0105 (M+H), found (M+H) 333.01046.

Following the procedure described above in Example 1, 4-(3,5-dichlorophenylamino)-6-fluoro-[1,7]naphthyridine-3-carbonitrile (300 mg, 1.1 mmol, 1 eq) was reacted with 2-morpholin-4-yl-1-ethylamine (3 mL, 20 eq). The crude product was purified via preparative HPLC to obtain 56 mg product (14% yield): HRMS (ESI+) calcd for $C_{21}H_{20}Cl_2FN_6O$ 443.1149 (M+H). found. (M+H) 443.1139.

Example 68

4-[(3,5-dichlorophenyl)amino]-6-{[(1R)-1-phenylethyl)amino]}-1,7-naphthyridine-3-carbonitrile Following the procedure described above in Example 1, 4-[(3,5-dichlorophenyl)amino]-6-fluoro-[1,7]naphthyridine-3-carbonitrile (300 mg, 1.1 mmol, 1 eq) was reacted with (1R)-1-phenylethyl)amine (3 mL, 20 eq). The crude product was purified via preparative HPLC to obtain 87 mg product (22% yield): HRMS (ESI+) calcd for $C_{21}H_{20}Cl_2N_5$ 434.0934 (M+H), found (M+H) 434.0927.

Example 69

4-[(3,5-dichlorophenyl)amino]-6-[(pyridin-3-ylmethyl)amino]-1,7-naphthyridine-3-carbonitrile Following the procedure described above in Example 1, 4-(3,5-dichlorophenylamino)-6-fluoro-[1,7]naphthyridine-3-carbonitrile (300 mg, 1.1 mmol, 1 eq) was reacted with pyridine-3-ylmethylamine (2.8 mL, 20 eq). The crude product was purified via preparative HPLC to obtain 31 mg product (8% yield): HRMS (ESI+) calcd for $C_{21}H_{14}Cl_2N_6$ 421.0730 (M+H), found (M+H) 421.0721.

Example 70

4-(4-Chloro-3-fluoro-phenylamino)-6-((R)1,2,3,4-tetrahydro-naphthalen-1-ylamino)-[1,7]naphthyridine-3-carbonitrile Following the procedure described above in Example 1, 4-(4-Chloro-3-fluoro-phenylamino)-6-fluoro-[1,7]naphthyridine-3-carbonitrile (150 mg, 0.47 mmol, 1 eq) was reacted with (R)-1,2,3,4-tetrahydro-1-naphthylamine (1.36 mL, 9.49 mmol, 20 eq). The crude product was purified via preparative HPLC to obtain 58 mg product (28% yield): 1H NMR (400 MHz, DMSO-D6) δ ppm 1.74-1.89 (m, 2 H) 1.91-2.07 (m, 2 H) 2.71-2.87 (m, 2 H) 5.09-5.18 (m, 1 H) 7.08-7.20 (m, 4 H) 7.20-7.28 (m, 2 H) 7.28-7.34 (m, 1 H) 7.44 (t, J=8.97 Hz, 1 H) 7.55 (dd, J=6.06, 1.77 Hz, 1 H) 8.27 (s, 1 H) 8.87 (s, 1 H) 9.65 (s, 1 H).

Example 71

4-(4-Chloro-3-fluoro-phenylamino)-6-((S) 1,2,3,4-tetrahydro-naphthalen-1-ylamino)-[1,7]naphthyridine-3-carbonitrile Following the procedure described above in Example 1, 4-(4-Chloro-3-fluoro-phenylamino)-6-fluoro-[1,7]naphthyridine-3-carbonitrile (150 mg, 0.47 mmol) was reacted with (S)-1,2,3,4-tetrahydro-1-naphthylamine (1.36 mL, 9.49 mmol, 20 eq) to obtain 67 mg product (31% yield): $^1$H NMR (400 MHz, DMSO-D6) δ ppm 1.71-1.90 (m, 2 H) 1.92-2.07 (m, 2 H) 2.71-2.84 (m, 2 H) 5.13 (s, 1 H) 7.08-7.19 (m, 4 H) 7.20-7.28 (m, 2 H) 7.29-7.35 (m, 1 H) 7.45 (t, J=9.09 Hz, 1 H) 7.57 (dd, J=6.32, 2.27 Hz, 1 H) 8.28 (s, 1 H) 8.89 (s, 1 H) 9.63 (s, 1 H).

Example 72

4-(4-Chloro-3-fluoro-phenylamino)-6-((S)-indan-1-ylamino)-[1,7]naphthyridine-3-carbonitrile Following the procedure described above in Example 1, 4-(4-Chloro-3-fluoro-phenylamino)-6-fluoro-[1,7]naphthyridine-3-carbonitrile (150 mg, 0.47 mmol, 1 eq) was reacted with (S)-(+)-1-aminoindan (1.21 mL, 9.49 mmol, 20 eq) to obtain 59 mg product (29% yield): 1H NMR (400 MHz, DMSO-D6) δ ppm 1.89-2.00 (m, 1 H) 2.52-2.61 (m, 1 H) 2.79-2.89 (m, 1 H) 2.94-3.04 (m, 1 H) 5.39-5.49 (m, 1 H) 7.13-7.19 (m, 1 H) 7.19-7.25 (m, 3 H) 7.25-7.31 (m, 2 H) 7.31-7.36 (m, 1 H) 7.46 (t, J=8.84 Hz, 1 H) 7.58 (dd, J=6.32, 2.27 Hz, 1 H) 8.30 (s, 1 H) 8.90 (s, 1 H) 9.67 (s, 1 H).

Example 73

4-(4-Chloro-3-fluoro-phenylamino)-6-((R)-(−)-indan-1-ylamino)-[1,7]naphthyridine-3-carbonitrile Following the procedure described above in Example 1, 4-(4-Chloro-3-fluoro-phenylamino)-6-fluoro-[1,7]naphthyridine-3-carbonitrile (150 mg, 0.47 mmol, 1 eq) was reacted with (R)-(−)-1-aminoindan (1.21 mL, 9.49 mmol, 20 eq) to obtain 45 mg product (22% yield): 1H NMR (400 MHz, DMSO-D6) δ ppm 1.88-1.99 (m, 1 H) 2.53-2.61 (m, 1 H) 2.79-2.89 (m, 1 H) 2.94-3.04 (m, 1 H) 5.40-5.48 (m, 1 H) 7.13-7.19 (m, 1 H) 7.19-7.25 (m, 3 H) 7.25-7.31 (m, 2 H) 7.31-7.37 (m, 1 H) 7.46 (t, J=8.97 Hz, 1 H) 7.59 (dd, J=6.06, 2.27 Hz, 1 H) 8.30 (s, 1 H) 8.89 (d, J=0.51 Hz, 1 H) 9.67 (s, 1 H).

Example 74

4-(4-Chloro-3-fluoro-phenylamino)-6-[((S)-(−)-1-ethyl-pyrrolidin-2-ylmethyl)-amino]-[1,7]naphthyridine-3-carbonitrile Following the procedure described above in Example 1, 4-(4-Chloro-3-fluoro-phenylamino)-6-fluoro-[1,7]naphthyridine-3-carbonitrile (150 mg, 0.47 mmol, 1 eq) was reacted with (S)-(−)-2-aminomethyl-1-ethylpyrrolidine (0.608 mL, 4.75 mmol, 10 eq) to obtain 73 mg product (36% yield): 1H NMR (400 MHz, DMSO-D6) δ ppm 1.04 (t, J=7.07 Hz, 3 H) 1.54-1.72 (m, 3 H) 1.84-1.93 (m, 1 H) 2.12-2.20 (m, 1 H) 2.26 (dd, J=11.87, 6.82 Hz, 1 H) 2.65-2.72 (m, 1 H) 2.88 (dd, J=11.75, 7.20 Hz, 1 H) 3.06-3.18 (m, 2 H) 3.35-3.42 (m, 1 H) 6.59 (t, J=5.56 Hz, 1 H) 7.02 (s, 1 H) 7.29-7.35 (m, 1 H) 7.46 (t, J=9.09 Hz, 1 H) 7.57 (dd, J=6.32, 2.78 Hz, 1 H) 8.20 (s, 1 H) 8.27 (s, 1 H) 8.83 (s, 1 H).

Example 75

4-(4-Chloro-3-fluoro-phenylamino)-6-[((R)-(+)-1-ethyl-pyrrolidin-2-ylmethyl)-amino]-[1,7]naphthyridine-3-carbonitrile Following the procedure described above in Example 1, 4-(4-Chloro-3-fluoro-phenylamino)-6-fluoro-[1,7]naphthyridine-3-carbonitrile (150 mg, 0.47 mmol, 1 eq) was reacted with (R)-(+)-2-aminomethyl-1-ethylpyrrolidine (0.608 mL, 4.75 mmol, 10 eq) to obtain 86 mg product (42% yield): 1H NMR (400 MHz, DMSO-D6) δ ppm 1.04 (t, J=7.20 Hz, 3 H) 1.55-1.72 (m, 3 H) 1.85-1.94 (m, 1 H) 2.17 (q, J=8.25 Hz, 1 H) 2.23-2.32 (m, 1 H) 2.65-2.74 (m, 1 H) 2.84-2.94 (m, 1 H) 3.07-3.18 (m, 2 H) 3.35-3.42 (m, 1 H) 6.60 (t, J=5.68 Hz, 1 H) 7.02 (s, 1 H) 7.29-7.35 (m, 1 H) 7.46 (t, J=8.97 Hz, 1 H) 7.57 (dd, J=6.57, 2.53 Hz, 1 H) 8.19 (s, 1 H) 8.27 (s, 1 H) 8.83 (s, 1 H).

Example 78

4-(3-iodophenylamino)-6-(2-morpholinoethylamino)-1,7-naphthyridine-3-carbonitrile Following the procedure described above in Example 1, 4-chloro-6-fluoro-1,7-naphthyridine-3-carbonitrile (0.35 g, 1.69 mmol) was reacted with 3-iodo-aniline (0.225 mL, 1.87 mmol, 1.1 eq) 2-ethoxyethanol (5 mL). After column chromatography (10-20% ethyl acetate in hexane), 575 mg 6-fluoro-4-(3-iodophenylamino)-1,7-naphthyridine-3-carbonitrile was obtained (44% yield): 1H NMR (400 MHz, DMSO-D6) δ ppm 7.25 (t, J=7.96 Hz, 1 H) 7.40 (ddd, J=8.08, 2.15, 0.88 Hz, 1 H) 7.67 (dt, J=7.83, 1.26 Hz, 1 H) 7.75 (t, J=1.77 Hz, 1 H) 8.15 (s, 1 H) 8.72 (s, 1 H) 9.09 (s, 1 H) 10.10 (s, 1 H).

Following the procedure described above in Example 1, 6-fluoro-4-(3-iodophenylamino)-1,7-naphthyridine-3-carbonitrile (1.46 g, 3.74 mmol, 1 eq) was reacted with 4-(2-aminoethyl)morpholine (10 mL, 76.2 mmol, 20 eq) in tetrahydrofuran (10 mL). Workup and flash column chromatography eluting with 3-6% methyl alcohol in dichloromethane yielded 4-(3-iodophenylamino)-6-(2-morpholinoethylamino)-1,7-naphthyridine-3-carbonitrile in 17% yield. 1H NMR (400 MHz, DMSO-D6) δ ppm 2.43 (s, 4 H) 2.55 (t, J=6.44 Hz, 2 H) 3.36 (q, J=6.15 Hz, 2 H) 3.53-3.61 (m, 4 H) 6.66 (t, J=5.43 Hz, 1 H) 6.97 (s, 1 H) 7.19 (t, J=7.83 Hz, 1 H) 7.25-7.31 (m, 1 H) 7.57 (d, J=8.08 Hz, 1 H) 7.62-7.65 (m, 1 H) 8.31 (s, 1 H) 8.86 (s, 1 H) 9.60 (s, 1 H).

Example 79

6-(2-morpholinoethylamino)-4-(3-(prop-1-ynyl)phenylamino)-1,7-naphthyridine-3-carbonitrile A mixture of 4-(3-iodophenylamino)-6-(2-morpholinoethylamino)-1,7-naphthyridine-3-carbonitrile (105.6 mg, 0.21 mmol, 1 eq) and tetrakis(triphenylphosphine)palladium(0) (25 mg, 0.02 mmol, 0.1 eq) was taken up in toluene (2.5 mL) in microwave tube. Tributyl(prop-1-ynyl)stannane (193 uL, 0.63 mmol, 3 eq) was added to the mixture. The tube was sealed and heated 150° C. for 1 hr. Work-up followed by chromatography (1-3% Methyl alcohol in dichloromethane), yielded 35.6 mg product (41% yield): 1H NMR (400 MHz, DMSO-D6) δ ppm 2.04 (s, 3 H) 2.40-2.46 (m, 4 H) 2.55 (t, J=6.69 Hz, 2 H) 3.30-3.40 (m, 2 H) 3.55-3.60 (m, 4 H) 6.64 (t, J=5.68 Hz, 1 H) 7.01 (s, 1 H) 7.23 (s, 1 H) 7.25 (s, 2 H) 7.34-7.40 (m, 1 H) 8.28 (s, 1 H) 8.84 (s, 1 H) 9.61 (s, 1 H).

Example 80

4-(3-(furan-2-yl)phenylamino)-6-(2-morpholinoethylamino)-1,7-naphthyridine-3-carbonitrile A mixture of 4-(3-iodophenylamino)-6-(2-morpholinoethylamino)-1,7-naphthyridine-3-carbonitrile (101.5 mg, 0.20 mmol, 1 eq) and tetrakis(triphenylphosphine)palladium(0) (25 mg, 0.02 mmol, 0.1 eq) was taken up in toluene (3 mL) in microwave tube. Tributyl(prop-1-ynyl)stannane (192 uL, 0.63 mmol, 3 eq) was added to the mixture. The tube was then sealed and heated 150° C. for 1 hr. Work-up followed by preparative HPLC yielded 56.3 mg product (63% yield): 1H NMR (400 MHz, acetonitrile-D3) δ ppm 2.47-2.73 (m, J=42.19 Hz, 6 H) 3.25-3.36 (m, 2 H) 3.51-3.62 (m, 4 H) 5.58 (s, 1 H) 6.39 (dd, J=3.54, 1.77 Hz, 1 H) 6.66 (d, J=3.28 Hz, 1 H) 6.69 (s, 1 H) 7.02-7.08 (m, 1 H) 7.27-7.33 (m, 1 H) 7.39-7.47 (m, 3 H) 7.98 (s, 1 H) 8.18 (s, 1 H) 8.76 (s, 1 H).

Example 81

6-(2-morpholinoethylamino)-4-(3-nitrophenylamino)-1,7-naphthyridine-3-carbonitrile Following the procedure described above in Example 1,4-chloro-6-fluoro-1,7-naphthyridine-3-carbonitrile (0.355 g, 1.71 mmol, 1 eq) was reacted with 3-nitroaniline (0.27 mL, 1.95 mmol, 1.1 eq) in 2-ethoxyethanol (4.5 mL). Column chromatography (15-20% ethyl acetate in hexane), yielded 676 mg 6-fluoro-4-(3-nitrophenylamino)-1,7-naphthyridine-3-carbonitrile (43% yield): $^1$H NMR (400 MHz, DMSO-D6) δ ppm 7.74 (t, J=8.08 Hz, 1 H) 7.80-7.85 (m, 1 H) 8.12-8.16 (m, 1 H) 8.17 (s, 1 H) 8.21 (t, J=2.02 Hz, 1 H) 8.80 (s, 1 H) 9.14 (s, 1 H) 10.35 (s, 1 H).

Following the procedure described above in Example 1,6-fluoro-4-(3-nitrophenylamino)-1,7-naphthyridine-3-carbonitrile (0.346 g, 1.12 mmol, 1 eq) was reacted with 4-(2-aminoethyl)morpholine (3 mL, 22.9 mmol, 20 eq) in tetrahydrofuran (2 mL). Workup and flash column chromatography eluting with 2-5% methyl alcohol in dichloromethane yielded 90.6 mg product (19% yield): 1H NMR (400 MHz, DMSO-D6) δ ppm 2.37-2.48 (m, 4 H) 2.52-2.59 (m, 2 H) 3.35-3.41 (m, 2 H) 3.54-3.61 (m, 4 H) 6.71-6.80 (m, 1 H) 6.96 (s, 1 H) 7.66-7.71 (m, 2 H) 8.00-8.05 (m, 1 H) 8.06-8.08 (m, 1 H) 8.40 (s, 1 H) 8.92 (s, 1 H) 9.89 (s, 1 H)

Example 82

4-(3-aminophenylamino)-6-(2-morpholinoethylamino)-1,7-naphthyridine-3-carbonitrile A mixture of 6-(2-morpholinoethylamino)-4-(3-nitrophenylamino)-1,7-naphthyridine-3-carbonitrile (120 mg, 0.29 mmol, 1 eq) and $SnCl_2.2H_2O$ (348 mg, 1.54 mmol, 5.3 eq) in ethyl alcohol (12 mL) was heated to reflux for 2.5 hr. After cooling to room temperature, water (10 mL) was added followed by sodium bicarbonate (500 mg). The mixture was stirred at room temperature for 1 hr. Ethyl acetate extraction followed by column chromatography (3-5% methyl alcohol in dichloromethane) yield 43 mg product (39% yield): 1H NMR (400 MHz, DMSO-D6) δ ppm 2.40-2.48 (m, 4 H) 2.53-2.60 (m, 2 H) 3.34-3.40 (m, 2 H) 3.54-3.63 (m, 4 H) 5.18-5.27 (m, 2 H) 6.39-6.47 (m, 3 H) 6.57 (s, 1 H) 7.01-7.08 (m, 2 H) 8.22 (s, 1 H) 8.81 (s, 1 H) 9.43 (s, 1 H).

Example 83

Methyl 3-(3-cyano-6-(2-morpholinoethylamino)-1,7-naphthyridin-4-ylamino)benzoate Following the procedure described above in Example 1,4-chloro-6-fluoro-1,7-naphthyridine-3-carbonitrile (0.360 g, 1.73 mmol, 1 eq) was reacted with methyl 3-aminobenzoate (0.288 mL, 1.91 mmol, 1.1 eq) in 2-ethoxyethanol (5 mL). Column chromatography (10-20% ethyl acetate in hexane) yielded 516.5 mg methyl 3-(3-cyano-6-fluoro-1,7-naphthyridin-4-ylamino)benzoate (31% yield): 1H NMR (400 MHz, DMSO-D6) δ ppm 3.88 (s, 3 H) 7.62 (t, J=7.71 Hz, 1 H) 7.64-7.69 (m, J=8.46, 1.89, 1.52 Hz, 1 H) 7.88-7.93 (m, 2 H) 8.19 (s, 1 H) 8.72 (s, 1 H) 9.10 (s, 1 H) 10.22 (s, 1 H).

Following the procedure described above in Example 1, methyl 3-(3-cyano-6-fluoro-1,7-naphthyridin-4-ylamino)benzoate (0.25 g, 0.78 mmol, 1 eq) was reacted with 4-(2-aminoethyl)morpholine (1 mL, 7.62 mmol, 9.8 eq) in tetrahydrofuran (4 mL). Workup and flash column chromatography eluting with 2-5% methyl alcohol in dichloromethane yielded 539 mg product (54% yield): 1H NMR (400 MHz, DMSO-D6) δ ppm 2.40-2.46 (m, 4 H) 2.55 (t, J=6.44 Hz, 2 H) 3.34-3.39 (m, 2 H) 3.54-3.60 (m, 4 H) 3.87 (s, 3 H) 6.67 (t, J=5.18 Hz, 1 H) 7.01 (s, 1 H) 7.56 (dt, J=4.36, 1.23 Hz, 2 H) 7.79-7.83 (m, 2 H) 8.32 (s, 1 H) 8.87 (s, 1 H) 9.73 (s, 1 H).

Example 84

3-(3-cyano-6-(2-morpholinoethylamino)-1,7-naphthyridin-4-ylamino)benzoic acid

To methyl 3-(3-cyano-6-(2-morpholinoethylamino)-1,7-naphthyridin-4-ylamino)benzoate in tetrahydrofuran (12 mL) was added methyl alcohol (4.5 mL) and lithium hydroxide (1 N, 4.5 mL). After 12 hr the solvents were evaporated and the crude mixture was purified by preparative HPLC to give 3-(3-cyano-6-(2-morpholinoethylamino)-1,7-naphthyridin-4-ylamino)benzoic acid in quantitative yield.

1H NMR (400 MHz, MeOD) δ ppm 3.13-3.23 (m, 6 H) 3.72 (t, J=6.06 Hz, 2 H) 3.84-3.90 (m, 4 H) 7.09 (s, 1 H) 7.48-7.55 (m, 2 H) 7.90-7.96 (m, 2 H) 8.29 (s, 1 H) 8.90 (s, 1 H).

Example 85

N-(3-(3-cyano-6-(2-morpholinoethylamino)-1,7-naphthyridin-4-ylamino)phenyl)methanesulfonamide 4-(3-aminophenylamino)-6-(2-morpholinoethylamino)-1,7-naphthyridine-3-carbonitrile (111 mg, 0.29 mmol, 1 eq) was suspended in methylene chloride (10 mL). Triethylamine (44 uL, 0.32 mmol, 1.1 eq) was added and the mixture was cooled to 0° C. Methylsulfonyl chloride (24 uL, 0.31 mmol, 1.1 eq) was added and the mixture was stirred at room temperature for 12 hr. Another 44 uL triethylamine (1.1 eq) and 48 uL methylsulfonyl chloride (2.2 eq) were added and reaction mixture was stirred for 12 hr. Work-up and preparative HPLC yielded 45.5 mg product (34% yield): 1H NMR (400 MHz, DMSO-D6) δ ppm 2.39-2.47 (m, 4 H) 2.56 (t, J=6.82 Hz, 2 H) 2.99-3.03 (m, 3 H) 3.27-3.42 (m, 2 H) 3.55-3.61 (m, 4 H) 6.63 (t, J=6.06 Hz, 1 H) 7.00-7.04 (m, 1 H) 7.04 (s, 1 H) 7.08 (d, J=8.59 Hz, 1 H) 7.12-7.16 (m, 1 H) 7.36 (t, J=8.34 Hz, 1 H) 8.26 (s, 1 H) 8.84 (s, 1 H) 9.69 (s, 2 H).

Example 86

3-(3-cyano-6-(2-morpholinoethylamino)-1,7-naphthyridin-4-ylamino)benzamide

Following the procedure described above in Example 1,4-chloro-6-fluoro-1,7-naphthyridine-3-carbonitrile (0.360 g, 1.73 mmol, 1 eq) was reacted with 3-aminobenzamide (0.260 mL, 1.91 mmol, 1.1 eq) in 2-ethoxyethanol (5 mL). Column chromatography (5% methyl alcohol in dichloromethane) yielded 231 mg 3-(3-cyano-6-fluoro-1,7-naphthyridin-4-ylamino)benzamide (43% yield): $^1$H NMR (400 MHz, DMSO-D6) δ ppm 7.00-7.08 (m, 1 H) 7.49-7.59 (m, 2 H) 7.81-7.92 (m, 2 H) 8.04 (s, 1 H) 8.21 (s, 1 H) 8.70 (s, 1 H) 9.09 (s, 1 H) 10.18 (s, 1 H).

Following the procedure described above in Example 1,3-(3-cyano-6-fluoro-1,7-naphthyridin-4-ylamino)benzamide (0.23 g, 0.78 mmol, 1 eq) was reacted with 4-(2-aminoethyl)morpholine (2 mL, 15.2 mmol, 20 eq) in tetrahydrofuran (3 mL). Workup and flash column chromatography eluting with 2.5-5% methyl alcohol in dichloromethane yielded 116.6 mg product (37% yield): 1H NMR (400 MHz, DMSO-D6) δ ppm 2.38-2.48 (m, 4 H) 2.52-2.59 (m, 2 H) 3.34-3.41 (m, 2 H) 3.53-3.62 (m, 4 H) 6.64 (s, 1 H) 7.05 (s, 1 H) 7.40-7.52 (m, 3 H) 7.73-7.81 (m, 2 H) 8.02 (s, 1 H) 8.29 (s, 1 H) 8.86 (s, 1 H) 9.69 (s, 1 H).

Example 87

4-(1,1'-biphenyl-4-ylamino)-6-[(2-morpholin-4-yl-ethyl)amino]-1,7-naphthyridine-3-carbonitrile

Following the procedure described above in Example 1,4-chloro-6-fluoro-1,7-naphthyridine-3-carbonitrile (0.281 g, 1.35 mmol, 1 eq) was reacted with 4-aminobiphenyl (0.253 g, 1.50 mmol, 1.1 eq) in 2-ethoxyethanol (5 mL). Column chromatography (10-30% ethyl acetate in hexane) yielded 228.5 mg 4-(1,1'-biphenyl-4-ylamino)-6-fluoro-1,7-naphthyridine-3-carbonitrile (50% yield): 1H NMR (400 MHz, DMSO-D6) δ ppm 7.34-7.42 (m, 1 H) 7.42-7.54 (m, 4 H) 7.73-7.80 (m, 4 H) 8.22 (s, 1 H) 8.70 (s, 1 H) 9.09 (s, 1 H) 10.15 (s, 1 H)

Following the procedure described above in Example 1,4-(1,1'-biphenyl-4-ylamino)-6-fluoro-1,7-naphthyridine-3-carbonitrile (0.23 g, 0.68 mmol, 1 eq) was reacted with 4-(2-aminoethyl)morpholine (1 mL, 7.6 mmol, 10 eq) in tetrahydrofuran (4 mL). Workup and flash column chromatography eluting with 2-5% methyl alcohol in dichloromethane yielded 99 mg product (33% yield): $^1$H NMR (400 MHz, MeOD) δ ppm 3.24-3.54 (m, 6 H) 3.98-4.07 (m, 2 H) 4.14-4.24 (m, 4 H) 7.45 (s, 1 H) 7.69-7.75 (m, 1 H) 7.75-7.79 (m, 2 H) 7.82 (t, J7.58 Hz, 2 H) 8.04 (d, J=7.07 Hz, 2 H) 8.06-8.11 (m, 2 H) 8.68 (s, 1 H) 9.26 (s, 1 H).

Example 88

6-(2-morpholinoethylamino)-4-(4-nitrophenylamino)-1,7-naphthyridine-3-carbonitrile

Following the procedure described above in Example 1,4-chloro-6-fluoro-1,7-naphthyridine-3-carbonitrile (0.36 g, 1.73 mmol, 1 eq) was reacted with 4-nitroaniline (0.263 g, 1.90 mmol, 1.1 eq) in 2-ethoxyethanol (5 mL). Column chromatography (20-28% ethyl acetate in hexane) yielded 205 mg 6-fluoro-4-(4-nitrophenylamino)-1,7-naphthyridine-3-carbonitrile (38% yield).

Following the procedure described above in Example 1,6-fluoro-4-(4-nitrophenylamino)-1,7-naphthyridine-3-carbonitrile (0.205 g, 0.66 mmol, 1 eq) was reacted with 4-(2-aminoethyl)morpholine (1 mL, 7.6 mmol, 10 eq) in tetrahydrofuran (4 mL). Workup and flash column chromatography eluting with 2-4% methyl alcohol in dichloromethane yielded 51.4 mg product (18% yield): 1H NMR (400 MHz, DMSO-D6) δ ppm 2.35-2.42 (m, J=3.79 Hz, 4 H) 2.46-2.50 (m, 2 H) 3.34-3.39 (m, 2 H) 3.52-3.57 (m, 4 H) 6.78 (s, 1 H) 6.89 (t, J=5.56 Hz, 1 H) 7.23 (d, J=9.09 Hz, 2 H) 8.18-8.23 (m, J=9.73, 3.03, 2.65 Hz, 2 H) 8.54 (s, 1 H) 8.98 (s, 1 H) 10.12 (s, 1 H)

Example 89

4-((3-chloro-4-fluorophenyl)(methyl)amino)-6-(2-morpholinoethylamino)-1,7-naphthyridine-3-carbonitrile

A mixture of 4-(4-Chloro-3-fluoro-phenylamino)-6-fluoro-[1,7]naphthyridine-3-carbonitrile (318 mg, 1 mmol, 1 eq) and NaH (60% in mineral oil, 44 mg, 1.1 mmol, 1.1 eq) was dissolved in DMF (5 mL). After 10 min of vigorous stirring at room temperature, MeI (75 uL, 1.2 mmol, 1.2 eq) was added and the mixture was stirred for 12 hr. Ethyl acetate extraction and preparative HPLC yielded 233.8 mg 4-((3-chloro-4-fluorophenyl)(methyl)amino)-6-fluoro-1,7-naphthyridine-3-carbonitrile (71% yield): $^1$H NMR (400 MHz, DMSO-D6) δ ppm 3.83 (s, 3 H) 6.80-6.85 (m, J=8.59, 4.29, 2.53 Hz, 1 H) 7.03 (dd, J=6.57, 2.53 Hz, 1 H) 7.28-7.34 (m, 1 H) 7.86 (d, J=2.02 Hz, 1 H) 8.37 (s, 1 H) 8.72 (s, 1 H).

Following the procedure described above in Example 1,4-((3-chloro-4-fluorophenyl)(methyl)amino)-6-fluoro-1,7-naphthyridine-3-carbonitrile (0.200 g, 0.61 mmol, 1 eq) was reacted with 4-(2-aminoethyl)morpholine (1 mL, 7.6 mmol, 10 eq) in tetrahydrofuran (4 mL). Workup and preparative HPLC yielded 96.8 mg product (36% yield): $^1$H NMR (400 MHz, DMSO-D6) δ ppm 2.37-2.44 (m, 4 H) 2.44-2.48 (m, 2 H) 3.41 (q, J=6.32 Hz, 2 H) 3.55-3.60 (m, 4 H) 3.75 (s, 3 H) 6.77 (ddd, J=8.65, 4.36, 2.65 Hz, 1 H) 6.86 (t, J=5.31 Hz, 1 H) 6.95 (dd, J=6.82, 2.53 Hz, 1 H) 7.23-7.29 (m, 1 H) 7.32 (s, 1 H) 8.09 (s, 1 H) 8.49 (s, 1 H).

Example 90

4-(3-chloro-4-fluorophenylamino)-6-(cyclopropylamino)-1,7-naphthyridine-3-carbonitrile

Following the procedure described above in Example 1,4-(4-Chloro-3-fluoro-phenylamino)-6-fluoro-[1,7]naphthyridine-3-carbonitrile (196 mg, 0.62 mmol, 1 eq) was reacted with cyclopropylamine (0.215 mL, 3.08 mmol, 5 eq) in tetrahydrofuran (4 mL). The crude product was purified via preparative HPLC to obtain 3 mg product (1% yield): $^1$H NMR (400 MHz, DMSO-D6) δ ppm 0.41-0.56 (m, 2 H) 0.68-0.84 (m, 2 H) 2.08 (s, 1 H) 6.66 (s, 1 H) 7.15 (s, 1 H) 7.25 (s, 1 H) 7.30-7.38 (m, 1 H) 7.47 (t, J=8.97 Hz, 1 H) 7.54-7.63 (m, 1 H) 8.29 (s, 1 H) 8.83 (s, 1 H).

Example 91

4-(3-chloro-4-fluorophenylamino)-6-(tert-pentylamino)-1,7-naphthyridine-3-carbonitrile

Following the procedure described above in Example 1,4-(4-Chloro-3-fluoro-phenylamino)-6-fluoro-[1,7]naphthyridine-3-carbonitrile (150 mg, 0.47 mmol, 1 eq) was reacted with tert-amylamine (3 mL). The crude product was purified via preparative HPLC to obtain 35.9 mg product (20% yield): $^1$H NMR (400 MHz, DMSO-D6) δ ppm 0.80 (t, J=7.45 Hz, 3 H) 1.30-1.40 (m, 6 H) 1.82 (q, J=7.49 Hz, 2 H) 6.30-6.42 (m, 1 H) 6.97 (s, 1 H) 7.20-7.29 (m, 1 H) 7.43 (t, J=9.09 Hz, 1 H) 7.45-7.51 (m, 1 H) 8.25 (s, 1 H) 8.81 (s, 1 H).

Example 92

6-(3-chloro-4-fluorophenylamino)-4-(cyclopentylamino)-1,7-naphthyridine-3-carbonitrile A mixture of 3-chloro-4-fluorobenzenamine (550 mg, 3.78 mmol, 38 eq), 4-(cyclopentylamino)-6-fluoro-1,7-naphthyridine-3-carbonitrile (28 mg, 0.1 mmol, 1 eq), and cesium carbonate (506 mg, 1.55 mmol, 15.5 eq) in DMF (4 mL) was heated to 200° C. in a microwave tube for 1 hr using microwave reactor. Preparative HPLC purification yielded 15 mg product (36% yield): $^1$H NMR (400 MHz, DMSO-D6) δ ppm 1.52-1.68 (m, 2 H) 1.70-1.91 (m, 4 H) 1.99-2.16 (m, 2 H) 4.58-4.76 (m, 1 H) 7.33 (t, J=9.09 Hz, 1 H) 7.45-7.56 (m, 1 H) 7.76 (s, 1 H) 7.80 (d, J=7.07 Hz, 1 H) 7.87-7.97 (m, 1 H) 8.32 (s, 1 H) 8.90 (s, 1 H) 9.64 (s, 1 H).

Example 93

6-(Benzyl-methyl-amino)-4-(3-chloro-4-fluoro-phenylamino)-[1,7]naphthyridine-3-carbonitrile Following the procedure described above in Example 1, 4-(3-Chloro-4-fluoro-phenylamino)-6-fluoro-[1,7]naphthyridine-3-carbonitrile (190 mg, 0.6 mmol, 1 eq) was reacted with benzyl methyl amine (1.46 g, 12 mmol, 20 eq). The crude product was purified via preparative HPLC to obtain 150 mg product (60% yield): $^1$H NMR (400 MHz, DMSO-D6) δ ppm 3.10 (s, 3 H) 4.98 (s, 2 H) 7.19-7.27 (m, 4 H) 7.27-7.41 (m, 3 H) 7.48 (t, J=8.97 Hz, 1 H) 7.63 (dd, J=6.69, 2.40 Hz, 1 H) 8.30 (s, 1 H) 8.94 (s, 1 H) 9.73 (s, 1 H).

Example 94

4-(3-Chloro-4-fluoro-phenylamino)-6-cyclopentylamino-[1,7]naphthyridine-3-carbonitrile Following the procedure described above in Example 1, 4-(3-Chloro-4-fluoro-phenylamino)-6-fluoro-[1,7]naphthyridine-3-carbonitrile (200 mg, 0.64 mmol, 1 eq) was reacted with cyclopentyl amine (1.26 ml, 12.8 mmol, 20 eq). The crude product was purified via preparative HPLC to obtain 80 mg product (33% yield): 1H NMR (400 MHz, DMSO-D6) δ ppm 1.43-1.63 (m, 4 H) 1.65-1.78 (m, 2 H) 1.91-2.07 (m, J=9.35 Hz, 2 H) 3.84-4.02 (m, 1 H) 6.81-6.98 (m, 2 H) 7.30-7.40 (m, 1 H) 7.41-7.53 (m, 1 H) 7.56-7.65 (m, 1 H) 8.26 (s, 1 H) 8.83 (s, 1 H) 9.63 (s, 1 H).

Example 95

4-Phenylamino-6-[(pyridin-3-ylmethyl)-amino]-[1,7] naphthyridine-3-carbonitrile

Following the procedure described above in Example 1, 4-Chloro-6-fluoro-[1,7]naphthyridine-3-carbonitrile (622 mg, 3.0 mmol, 1 eq) was reacted with aniline (0.3 ml, 3.3 mmol, 1.1 eq) in DME (8 mL). The crude product was recrystallized from ethyl acetate to obtain 634 mg 6-fluoro-4-phenylamino-[1,7]naphthyridine-3-carbonitrile (80% yield): $^1$H NMR (400 MHz, DMSO-D6) δ ppm 7.23-7.34 (m, 3 H) 7.42 (t, J=7.71 Hz, 2 H) 8.13 (s, 1 H) 8.52 (s, 1 H) 8.96 (s, 1 H) 10.15 (br, s, 1 H).

Following the procedure described above in Example 1, 6-fluoro-4-phenylamino-[1,7]naphthyridine-3-carbonitrile (373 mg, 1.42 mmol, 1 eq) was reacted with C-pyridin-3-yl-methylamine (2.9 ml, 28.4 mmol, 20 eq). The crude product was purified via preparative HPLC to obtain 249 mg product (50% yield): 1H NMR (400 MHz, DMSO-D6) δ ppm 4.56 (d, J=6.32 Hz, 2 H) 7.10-7.16 (m, 1 H) 7.22-7.30 (m, 3 H) 7.33 (dd, J=7.58, 4.80 Hz, 1 H) 7.41 (t, J=7.83 Hz, 2 H) 7.44-7.54 (m, 1 H) 7.75 (d, J=7.83 Hz, 1 H) 8.25 (s, 1 H) 8.39-8.48 (m, 1 H) 8.59 (s, 1 H) 8.85 (s, 1 H) 9.62 (s, 1 H).

Biological Testing

To determine whether Tpl2 inhibitors may be efficacious in the treatment of rheumatoid arthritis, as well as other inflammatory disease states, an N-terminal 6His-tagged human Cot/Tpl2 kinase construct encoding residues 30-398 was expressed in a baculovirus system (BD Biosciences, San Jose, Calif.). Sf9 cells expressing the kinase were lysed in 50 mM NaPhosphate pH=8; 300 mM NaCl; 5 mM imidazole; 0.1 mM EGTA; 25 mM beta-glycerophosphate; 1% TX-100, 1% glycerol; 6 mM beta-mercaptoethanol and protease inhibitors. The lysate was clarified by centrifugation and was loaded onto a Ni-Sepharose column. The column was washed with 50 mM NaPhosphate pH=8; 300 mM NaCl; 15 mM imidazole; 1% glycerol; and 6 mM beta-mercaptoethanol. His-Tpl2 was eluted with 50 mM NaPhosphate pH=8; 300 mM NaCl; 250 mM imidazole; 1% glycerol; and 6 mM beta-mercaptoethanol. The eluted protein was further purified by size exclusion chromatography. Fractions corresponding to monomeric Tpl2 were then used in the assay.

Tpl2/Cot activity was directly assayed using GST-MEK1 as a substrate. GST-MEK1 phosphorylation on serine residues 217 and 221 was detected by ELISA. 0.4 nM Tpl2 was incubated with 35 nM GST-MEK1 in a kinase reaction buffer containing 20 mM MOPS pH=7.2; 50 uM ATP; 20 mM $MgCl_2$; 1 mM DTT; 25 mM β-glycerophosphate; 5 mM EGTA; and 1 mM sodium orthovanadate for 1 h at 30° C. The compounds of the inventions solubilized in 100% DMSO were pre-diluted in assay buffer so that the final concentration of DMSO in the reaction was 1%. The kinase reaction was carried out in 100 ul volume on 96 well plates. The kinase reaction was then stopped with the addition of 100 mM EDTA. The entire reaction mix was then transferred to the detection plate, a 96 well Immunosorb plate that had been pre-coated with anti-GST antibody (Amersham). After a 1 hour incubation at room temperature, the detection plate was washed 4 times with TBST (TBS+0.05% Tween 20) and then incubated for another hour at room temperature with anti phospho-MEK1 antibody (Cell Signaling) 1:1000 in 10 mM MOPS 7.5; 150 mM NaCl; 0.05% Tween 20; 0.1% Gelatin; 0.02% $NaN_3$; and 1% BSA. The detection plate was washed again and incubated for 30 min with DELFIA Europium (Eu) labeled goat anti-rabbit IgG (Perkin-Elmer), 1:4000 in the same buffer used for the primary incubation. After a final wash, Eu detection solution was added to each well and the Eu signal was measured in a Wallac Victor$^2$ Multilabel Counter. $IC_{50}$ calculations were preformed using the XLfit software package (IDBS, Guildford, UK). $IC_{50}$ values for representative compounds according to the invention are listed in Table 1 below.

TABLE 1

| Example | IC$_{50}$ (μM) |
|---|---|
| 1 | 0.05 |
| 2 | 11.6 |
| 3 | 1.16 |
| 4 | 10.7 |
| 5 | >40 |
| 7 | 0.008 |
| 8 | >40 |
| 9 | 1.7 |
| 10 | 7.6 |
| 11 | 0.006 |
| 12 | 0.065 |
| 13 | 3.6 |
| 14 | 0.017 |
| 15 | >40 |
| 16 | >10 |
| 17 | >10 |
| 18 | >10 |
| 19 | 0.009 |
| 20 | 0.29 |
| 21 | 0.0096 |
| 22 | 0.079 |
| 23 | 0.036 |
| 24 | 1.12 |
| 25 | 0.038 |
| 26 | 10 |
| 27 | 4.6 |
| 28 | >40 |
| 29 | >40 |
| 30 | >40 |
| 31 | >40 |
| 32 | >40 |
| 33 | >40 |
| 34 | 1.5 |
| 35 | 5 |
| 36 | >40 |
| 37 | >40 |
| 38 | >40 |
| 39 | >40 |
| 40 | >40 |
| 41 | 0.3 |
| 42 | >40 |
| 43 | >40 |
| 44 | >40 |
| 45 | 20 |
| 47 | 0.1 |
| 48 | 5 |
| 49 | 3 |
| 50 | 40 |
| 51 | 0.41 |
| 52 | >40 |
| 53 | 7 |
| 54 | 1.3 |
| 55 | 1.5 |
| 56 | 3.6 |
| 57 | 36 |
| 58 | 3.7 |
| 59 | 0.012 |
| 60 | 2.4 |
| 61 | 10.5 |
| 62 | 10 |
| 63 | >40 |
| 64 | >40 |
| 65 | 6.2 |
| 66 | >40 |
| 67 | 4.2 |
| 68 | 0.94 |
| 69 | 4.1 |
| 70 | 1.5 |
| 71 | 3.9 |
| 72 | 1.5 |
| 73 | 0.43 |
| 74 | 0.18 |
| 75 | 7 |
| 78 | 7.1 |
| 79 | >10 |
| 80 | >10 |
| 81 | 0.27 |
| 82 | >10 |
| 83 | >10 |
| 84 | >10 |
| 85 | >10 |
| 86 | >10 |
| 87 | >40 |
| 88 | 7.0 |
| 89 | >40 |
| 90 | 10 |
| 91 | >40 |
| 92 | 8 |
| 93 | >40 |
| 94 | 7.6 |
| 95 | 0.33 |

Additional representative compounds of the invention made according to the methods described herein and their corresponding IC$_{50}$ values are listed in Table 2 below.

TABLE 2

| Example | Compound | IC$_{50}$ (μM) |
|---|---|---|
| 96 | 4-[(3-chloro-4-fluorophenyl)amino]-6-[(4-methoxybenzyl)amino]-1,7-naphthyridine-3-carbonitrile | 0.2 |
| 97 | 6-fluoro-4-[(3-isopropylphenyl)amino]-1,7-naphthyridine-3-carbonitrile | >40 |
| 98 | 4-[(3-chloro-4-fluorobenzyl)amino]-6-fluoro-1,7-naphthyridine-3-carbonitrile | >40 |
| 99 | 6-Fluoro-4-(4-phenoxy-phenylamino)-[1,7]naphthyridine-3-carbonitrile | 20 |
| 100 | 6-fluoro-4-{[4-(trifluoromethyl)phenyl]amino}-1,7-naphthyridine-3-carbonitrile | >40 |
| 101 | 6-fluoro-4-[(4-isopropylphenyl)amino]-1,7-naphthyridine-3-carbonitrile | >40 |
| 102 | 6-fluoro-4-(1H-indol-5-ylamino)-1,7-naphthyridine-3-carbonitrile | >40 |
| 103 | 6-amino-4-[(3-chloro-4-fluorophenyl)amino]-1,7-naphthyridine-3-carboxylic acid | >40 |
| 104 | 6-fluoro-4-[(3-iodophenyl)amino]-1,7-naphthyridine-3-carbonitrile | >40 |
| 105 | 6-fluoro-4-[(3-nitrophenyl)amino]-1,7-naphthyridine-3-carbonitrile | >10 |
| 106 | 4-[(4-benzylphenyl)amino]-6-fluoro-1,7-naphthyridine-3-carbonitrile | 0.3 |
| 107 | 4-[(3-chloro-4-fluorophenyl)(methyl)amino]-6-fluoro-1,7-naphthyridine-3-carbonitrile | >10 |
| 108 | 4-[(4-benzylphenyl)amino]-6-{[2-(dimethylamino)ethyl]amino}-1,7-naphthyridine-3-carbonitrile | >10 |
| 109 | 4-[(3-chloro-4-fluorophenyl)amino]-6-[(1-pyridin-2-ylethyl)amino]quinoline-3-carbonitrile | 0.064 |
| 110 | 4-(tert-butylamino)-6-[(pyridin-3-ylmethyl)amino]-1,7-naphthyridine-3-carbonitrile | 0.63 |
| 111 | 4-(cyclopropylamino)-6-[(pyridin-3-ylmethyl)amino]-1,7-naphthyridine-3-carbonitrile | 2.8 |
| 112 | 4-(cyclopentylamino)-6-[(pyridin-3-ylmethyl)amino]-1,7-naphthyridine-3-carbonitrile | 0.32 |
| 113 | 4-(cycloheptylamino)-6-[(pyridin-3-ylmethyl)amino]-1,7-naphthyridine-3-carbonitrile | 0.16 |
| 114 | 4-(cyclohexylamino)-6-[(pyridin-3-ylmethyl)amino]-1,7-naphthyridine-3-carbonitrile | 0.47 |
| 115 | 4-[(3-chloro-4-fluorophenyl)amino]-6-[(1-phenylethyl)amino]-1,7-naphthyridine-3-carbonitrile | >40 |
| 116 | 4-(piperidin-4-ylamino)-6-[(pyridin-3-ylmethyl)amino]-1,7-naphthyridine-3-carbonitrile | >40 |
| 117 | 6-(2-(4-benzylpiperazin-1-yl)ethylamino)-4-(3-chloro-4-fluorophenylamino)-1,7-naphthyridine-3-carbonitrile | 2.4 |
| 118 | 4-[(3-chloro-4-fluorophenyl)amino]-6-[(1-methyl-1-phenylethyl)amino]-1,7-naphthyridine-3-carbonitrile | 1.2 |
| 119 | 4-(3-chloro-4-fluorophenylamino)-6-(pyridin-4-ylmethylamino)-1,7-naphthyridine-3-carbonitrile | 0.031 |

TABLE 2-continued

| Example | Compound | IC$_{50}$ (μM) |
|---|---|---|
| 120 | 4-(2-(4-(3-chloro-4-fluorophenylamino)-3-cyano-1,7-naphthyridin-6-ylamino)ethyl)benzenesulfonamide | 0.23 |
| 121 | 6-[(3-bromobenzyl)amino]-4-[(3-chloro-4-fluorophenyl)amino]-1,7-naphthyridine-3-carbonitrile | 0.43 |
| 122 | 4-[(3-chloro-4-fluorophenyl)amino]-6-[(2-piperidin-1-ylethyl)amino]-1,7-naphthyridine-3-carbonitrile | 2.5 |
| 123 | 4-(3-chloro-4-fluorophenylamino)-6-(pyridin-2-ylmethylamino)-1,7-naphthyridine-3-carbonitrile | 0.13 |
| 124 | 4-[(3-chloro-4-fluorophenyl)amino]-6-[(2-methoxybenzyl)amino]-1,7-naphthyridine-3-carbonitrile | 0.37 |
| 125 | 4-[(3-chloro-4-fluorophenyl)amino]-6-{[4-(methylsulfonyl)benzyl]amino}-1,7-naphthyridine-3-carbonitrile | 0.023 |
| 126 | 4-[(3-chloro-4-fluorophenyl)amino]-6-[(2,6-dichlorobenzyl)amino]-1,7-naphthyridine-3-carbonitrile | 24.6 |
| 127 | 4,6-bis[(2,6-dichlorobenzyl)amino]-1,7-naphthyridine-3-carbonitrile | >40 |
| 128 | 6-fluoro-4-{[4-(trifluoromethoxy)phenyl]amino}-1,7-naphthyridine-3-carbonitrile | >40 |
| 129 | 4-(cyclopentylamino)-6-({[(2S)-1-ethylpyrrolidin-2-yl]methyl}amino)-1,7-naphthyridine-3-carbonitrile | 2.8 |
| 130 | 4-(tert-butylamino)-6-{[4-(methylsulfonyl)benzyl]amino}-1,7-naphthyridine-3-carbonitrile | 4.6 |
| 131 | 4,6-bis{[(1R)-1-phenylethyl]amino}-1,7-naphthyridine-3-carbonitrile | 0.56 |
| 132 | 4,6-bis{[4-(methylsulfonyl)benzyl]amino}-1,7-naphthyridine-3-carbonitrile | 16.9 |
| 133 | 4-(cycloheptylamino)-6-{[(1R)-1-phenylethyl]amino}-1,7-naphthyridine-3-carbonitrile | 0.92 |
| 134 | 6-[(3-cyanobenzyl)amino]-4-(cycloheptylamino)quinoline-3-carbonitrile | 2.5 |
| 135 | 4-[(1,1-dimethylpropyl)amino]-6-[(pyridin-3-ylmethyl)amino]-1,7-naphthyridine-3-carbonitrile | 0.1 |
| 136 | 4-[cycloheptyl(methyl)amino]-6-fluoro-1,7-naphthyridine-3-carbonitrile | 0.36 |
| 137 | 4-[cycloheptyl(methyl)amino]-6-{[(1R)-1-phenylethyl]amino}-1,7-naphthyridine-3-carbonitrile | >40 |
| 138 | 4-[(1,1-dimethylprop-2-ynyl)amino]-6-[(pyridin-3-ylmethyl)amino]-1,7-3-carbonitrile | >40 |
| 139 | 6-amino-4-[(3-tert-butyl-1-methyl-1H-pyrazol-5-yl)amino]quinoline-3-carbonitrile | 0.27 |
| 140 | 4-[(3-chloro-4-fluorophenyl)amino]-6-{[4(5)imidazolyl]amino}-1,7-naphthyridine-3-carbonitrile | 0.079 |
| 141 | 4-[(1,1-dimethylpropyl)amino]-6-fluoro-1,7-naphthyridine-3-carbonitrile | >40 |
| 142 | 4-[(1-ethynylcyclohexyl)amino]-6-fluoro-1,7-naphthyridine-3-carbonitrile | 28 |
| 143 | 6-(tert-butylamino)-4-[(3-chloro-4-fluorophenyl)amino]-1,7-naphthyridine-3-carbonitrile | >40 |
| 144 | 4-[(3-chloro-4-fluorophenyl)amino]-6-(cycloheptylamino)-1,7-naphthyridine-3-carbonitrile | 5.2 |
| 145 | 4,6-bis(pyridin-3-ylmethylamino)-1,7-naphthyridine-3-carbonitrile | >40 |

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:
1. A compound of formula (I):

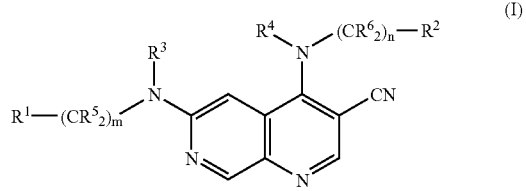

wherein:
R$^1$ is selected from the group consisting of C$_{3-10}$ cycloalkyl, aryl, 3-10 membered cycloheteroalkyl, and heteroaryl, each optionally substituted with 1-4 moieties selected from the group consisting of:
  a) halogen, b) CN, c) NO$_2$, d) N$_3$, e) OR$^7$, f) NR$^8$R$^9$, g) oxo, h) thioxo, i) S(O)$_p$R$^7$, j) SO$_2$NR$^8$R$^9$, k) C(O)R$^7$, l) C(O)OR$^7$, m) C(O)NR$^8$R$^9$, n) Si(C$_{1-6}$ alkyl)$_3$, o) C$_{1-6}$ alkyl, p) C$_{2-6}$ alkenyl, q) C$_{2-6}$ alkynyl, r) C$_{1-6}$ alkoxy, s) C$_{1-6}$ alkylthio, t) C$_{1-6}$ haloalkyl, u) C$_{3-10}$ cycloalkyl, v) aryl, w) 3-10 membered cycloheteroalkyl, and x) heteroaryl, wherein any of o)-x) optionally is substituted with 1-4 R$^{10}$ groups;

R$_2$ is selected from the group consisting of C$_{3-10}$ cycloalkyl, aryl, 3-10 membered cycloheteroalkyl, and heteroaryl, each optionally substituted with 1-4 moieties selected from the group consisting of:
  a) halogen, b) CN, c) NO$_2$, d) N$_3$, e) OR$^7$, f) NR$^8$R$^9$, g) oxo, h) thioxo, i) S(O)$_p$R$^7$, j) SO$_2$NR$^8$R$^9$, k) C(O)OR$^7$, l) C(O)OR$^7$, m) C(O)NR$^8$R$^9$, n) Si(C$_{1-6}$ alkyl)$_3$, o) C$_{1-6}$ alkyl, p) C$_{2-6}$ alkenyl, q) C$_{2-6}$ alkynyl, r) C$_{1-6}$ alkoxy, s) C$_{1-6}$ alkylthio, t) C$_{1-6}$ haloalkyl, u) C$_{3-10}$ cycloalkyl, v) aryl, w) 3-10 membered cycloheteroalkyl, and x) heteroaryl,
  wherein any of o)-x) optionally is substituted with 1-4 R$^{10}$ groups;

alternatively, R$^2$ is selected from the group consisting of halogen, C$_{1-6}$ alkyl optionally substituted with 1-4 R$^{10}$ groups, C$_{1-6}$ haloalkyl, NR$^8$R$^9$, OR$^7$, C(O)OR$^7$, C(O)NR$^8$R$^9$, S(O)$_p$R$^7$ and N$_3$;

R$_3$ and R$_4$ independently are selected from the group consisting of:
  a) H, b) C(O)R$^7$, c) C(O)OR$^7$, d) C(O)NR$^8$R$^9$, e) C$_{1-6}$ alkyl, f) C$_{2-6}$ alkenyl, g) C$_{2-6}$ alkynyl, h) C$_{1-6}$ haloalkyl, i) C$_{3-10}$ cycloalkyl, j) aryl, k) 3-10 membered cycloheteroalkyl, and l) heteroaryl,
  wherein any of e)-l) optionally is substituted with 1-4 R$^{10}$ groups;

R$^5$ and R$^6$ at each occurrence independently are selected from the group consisting of:
  a) H, b) halogen, c) OR$^7$, d) NR$^8$R$^9$, e) C$_{1-6}$ alkyl, f) C$_{2-6}$ alkenyl, g) C$_{2-6}$ alkynyl, h) C$_{1-6}$ haloalkyl, and i) aryl;
alternatively, any two R$^5$ or R$^6$ groups and the carbon to which they are bonded may form a carbonyl group;

R$^7$ at each occurrence is selected from the group consisting of:
  a) H, b) C(O)R$^{11}$, c) C(O)OR$^{11}$, d) C(O)NR$^{11}$R$^{12}$, e) C$_{1-6}$ alkyl f) C$_{2-6}$ alkenyl, g) C$^{2-6}$ alkynyl, h) C$_{1-6}$ haloalkyl, i) C$_{3-10}$ cycloalkyl, j) aryl, k) 3-10 membered cycloheteroalkyl, and l) heteroaryl;
  wherein any of e)-l) optionally is substituted with 1-4 R$^{13}$ groups;

R$^8$ and R$^9$ at each occurrence independently are selected from the group consisting of:

a) H, b) OR$^{11}$, c) SO$_2$R$^{11}$, d) C(O)R$^{11}$, e) C(O)OR$^{11}$, f) C(O)NR$^{11}$R$^{12}$, g) C$_{1-6}$ alkyl, h) C$_{2-6}$ alkenyl, i) C$_{2-6}$ alkynyl, j) C$_{1-6}$ haloalkyl, k) C$_{3-10}$ cycloalkyl, l) aryl, m) 3-10 membered cycloheteroalkyl, and n) heteroaryl;

wherein any of g)-n) optionally is substituted with 1-4 R$^{13}$ groups;

R$^{10}$ at each occurrence independently is selected from the group consisting of:

a) halogen, b) CN, c) NO$_2$, d) N$_3$, e) OR$^7$, f) NR$^8$R$^9$, g) oxo, h) thioxo, i) S(O)$_p$R$^7$, j) SO$_2$NR$^8$R$^9$, k) C(O)R$^7$, l) C(O)OR$^7$, m) C(O)NR$^8$R$^9$, n) Si(C$_{1-6}$ alkyl)$_3$, o) C$_{1-6}$ alkyl, p) C$_{2-6}$ alkenyl, q) C$_{2-6}$ alkynyl, r) C$_{1-6}$ alkoxy, s) C$_{1-6}$ alkylthio, t) C$_{1-6}$ haloalkyl, u) C$_{3-10}$ cycloalkyl, v) aryl, w) 3-10 membered cycloheteroalkyl, and x) heteroaryl, wherein any of o)-x) optionally is substituted with 1-4 R$^{13}$ groups;

R$^{11}$ and R$^{12}$ at each occurrence independently are selected from the group consisting of:

a) H, b) C$_{1-6}$ alkyl, c) C$_{2-6}$ alkenyl, d) C$_{2-6}$ alkynyl, e) C$_{1-6}$ haloalkyl, f) C$_{3-10}$ cycloalkyl, g) aryl, h) 3-10 membered cycloheteroalkyl, and i) heteroaryl, wherein any of b)-i) optionally is substituted with 1-4 R$^{13}$ groups;

R$^{13}$ at each occurrence independently is selected from the group consisting of:

a) halogen, b) CN, c) NO$_2$, d) N$_3$, e) OH, f) O—C$_{1-6}$ alkyl, g) NH$_2$, h) NH(C$_{1-6}$ alkyl), i) N(C$_{1-6}$ alkyl)$_2$, j) NH(aryl), k) NH(cycloalkyl), l) NH(heteroaryl), m) NH(cycloheteroalkyl), n) oxo, o) thioxo, p) SH, q) S(O)$_p$—C$_{1-6}$ alkyl, r) C(O)—C$_{1-6}$ alkyl, s) C(O)OH, t) C(O)O—C$_{1-6}$ alkyl, u) C(O)NH$_2$, v) C(O)NHC$_{1-6}$ alkyl, w) C(O)N(C$_{1-6}$ alkyl)$_2$, x) C$_{1-6}$ alkyl, y) C$_{2-6}$ alkenyl, z) C$_{2-6}$ alkynyl, aa) C$_{1-6}$ alkoxy, bb) C$_{1-6}$ alkylthio, cc) C$_{1-6}$ haloalkyl, dd) C$_{3-10}$ cycloalkyl, ee) aryl, ff) 3-10 membered cycloheteroalkyl, and gg) heteroaryl, wherein any C$_{1-6}$ alkyl, C$_{2-6}$ alkenyl, C$_{2-6}$ alkynyl, C$_{3-10}$ cycloalkyl, aryl, 3-10 membered cycloheteroalkyl, or heteroaryl, alone as a part of another moiety, optionally is substituted with one or more moieties selected from the group consisting of halogen, CN, NO$_2$, OH, O—C$_{1-6}$ alkyl, NH$_2$, NH(C$_{1-6}$ alkyl), N(C$_{1-6}$ alkyl)$_2$, NH(aryl), NH(cycloalkyl), NH(heteroaryl), NH(cycloheteroalkyl), oxo, thioxo, SH, S(O)$_p$—C$_{1-6}$ alkyl, C(O)—C$_{1-6}$ alkyl, C(O)OH, C(O)O—C$_{1-6}$ alkyl, C(O)NH$_2$, C(O)NHC$_{1-6}$ alkyl, C(O)N(C$_{1-6}$ alkyl)$_2$, C$_{1-6}$ alkyl, C$_{2-6}$ alkenyl, C$_{2-6}$ alkynyl, C$_{1-6}$ alkoxy, C$_{1-6}$ alkylthio, C$_{1-6}$ haloalkyl, C$_{3-10}$ cycloalkyl, aryl, 3-10 membered cycloheteroalkyl, and heteroaryl;

m is 0, 1, 2, 3, or 4;

n is 0 or 1; and p is 0, 1, or 2;

or a pharmaceutically acceptable salt thereof provided that the compound of formula (I) does not comprise 4-(3-bromo-phenylamino)-6-(4-methoxy-benzylamino)-[1,7] naphthyridine-3-carbonitrile or 4-(3-bromo-phenylamino)-6-(2-morpholin-4-yl-ethylamino)-[1,7] naphthyridine-3-carbonitrile.

2. The compound according to claim 1, wherein R$^1$ is a 5 or 6 membered heteroaryl.

3. The compound according to claim 2, wherein R$^1$ is imidazole.

4. The compound according to claim 2, wherein R$^1$ is pyridine.

5. The compound according to claim 4, wherein R$^1$ is pyridin-3-yl.

6. The compound according to claim 1, wherein R$^1$ is a 5 or 6 membered hetyerocycloalkyl.

7. The compound according to claim 6, wherein R$^1$ is piperazine.

8. The compound according to claim 6, wherein R$^1$ is morpholine.

9. The compound according to claim 1, wherein R$^1$ is phenyl optionally substituted with 1-4 moieties selected from the group consisting of:

a) halogen, b) CN, c) NO$_2$, d) N$_3$, e) OR$^7$, f) NR$^8$R$^9$, g) oxo, h) thioxo, i) S(O)$_p$R$^7$, j) SO$_2$NR$^8$R$^9$, k) C(O)R$^7$, l) C(O)OR$^7$, m) C(O)NR$^8$R$^9$, n) Si(C$_{1-6}$ alkyl)$_3$, o) C$_{1-6}$ alkyl, p) C$_{2-6}$ alkenyl, q) C$_{2-6}$ alkynyl, r) C$_{1-6}$ alkoxy, s) C$_{1-6}$ alkylthio, t) C$_{1-6}$ haloalkyl, u) C$_{3-10}$ cycloalkyl, v) aryl, w) 3-10 membered cycloheteroalkyl, and x) heteroaryl, wherein any of o)-x) optionally is substituted with 1-4 R$^{10}$ groups.

10. The compound according to claim 9, wherein R$^1$ is phenyl substituted with one or moieties selected from the group consisting of OR$^7$ and S(O)$_p$R$^7$.

11. The compound according to claim 10, wherein R$^1$ is phenyl substituted with OCH$_3$.

12. The compound according to claim 10, wherein R$^1$ is phenyl substituted with SO$_2$CH$_3$.

13. The compound according to claim 1, wherein m is 1.

14. The compound according to claim 1, wherein m is 2.

15. The compound according to claim 1, wherein R$^2$ is phenyl.

16. The compound according to claim 15, wherein R$^2$ is phenyl substituted with 1 or 2 halogens.

17. The compound according to claim 16, wherein R$^2$ is phenyl substituted with Cl.

18. The compound according to claim 16, wherein R$^2$ is phenyl substituted with F.

19. The compound according to claim 16, wherein R$^2$ is phenyl substituted with Cl and F.

20. The compound according to claim 19, wherein R$^2$ is 3-chloro-4-fluorophenyl.

21. The compound according to claim 15, wherein R$^2$ is phenyl substituted with benzyl.

22. The compound according to claim 15, wherein R$^2$ is phenyl substituted with S-phenyl.

23. The compound according to claim 15, wherein R$^2$ is phenyl substituted with O-phenyl.

24. The compound according to claim 1, wherein R$^2$ is cycloalkyl.

25. The compound according to claim 24, wherein R$^2$ is selected from the group consisting of cyclopropyl, cyclopentyl, cyclohexyl, and cycloheptyl.

26. The compound according to claim 1, wherein n is 0.

27. The compound according to claim 1, wherein R$^5$ is H.

28. The compound according to claim 1, wherein R$^5$ is C$_{1-6}$ alkyl.

29. The compound according to claim 1, wherein R$^6$ is H.

30. The compound according to claim 1, wherein R$^6$ is C$_{1-6}$ alkyl.

31. A pharmaceutical composition comprising one or more compounds according to claim 1, or pharmaceutically salts thereof, and one or more pharmaceutically acceptable carriers.

* * * * *